(12) United States Patent
Nakada et al.

(10) Patent No.: US 10,632,084 B2
(45) Date of Patent: Apr. 28, 2020

(54) AQUAPORIN 4 FUNCTION PROMOTOR AND PHARMACEUTICAL COMPOSITION FOR NEUROLOGICAL DISORDERS

(71) Applicant: NIIGATA UNIVERSITY, Niigata (JP)

(72) Inventors: Tsutomu Nakada, Niigata (JP); Vincent Huber, Niigata (JP); Hironaka Igarashi, Tokyo (JP); Yuji Suzuki, Zushi (JP); Ingrid Kwee, Moraga, CA (US)

(73) Assignee: NIIGATA UNIVERSITY, Niigata-Shi, Niigata (JP)

( * ) Notice: Subject to any disclaimer, the term of this patent is extended or adjusted under 35 U.S.C. 154(b) by 0 days.

(21) Appl. No.: 16/081,267

(22) PCT Filed: Mar. 3, 2017

(86) PCT No.: PCT/JP2017/008485
§ 371 (c)(1),
(2) Date: Aug. 30, 2018

(87) PCT Pub. No.: WO2017/150704
PCT Pub. Date: Sep. 8, 2017

(65) Prior Publication Data
US 2019/0091182 A1 Mar. 28, 2019

(30) Foreign Application Priority Data
Mar. 4, 2016 (JP) .................................. 2016-042766

(51) Int. Cl.
| | | |
|---|---|---|
| *A61K 31/155* | (2006.01) | |
| *A61K 31/443* | (2006.01) | |
| *A61K 31/4439* | (2006.01) | |
| *A61K 31/4433* | (2006.01) | |
| *A61K 31/44* | (2006.01) | |
| *A61P 25/28* | (2006.01) | |
| *A61P 35/00* | (2006.01) | |

(52) U.S. Cl.
CPC ............ *A61K 31/155* (2013.01); *A61K 31/44* (2013.01); *A61K 31/443* (2013.01); *A61K 31/4433* (2013.01); *A61K 31/4439* (2013.01); *A61P 25/28* (2018.01); *A61P 35/00* (2018.01)

(58) Field of Classification Search
CPC . A61K 31/155; A61K 31/443; A61K 31/4439
See application file for complete search history.

(56) References Cited

U.S. PATENT DOCUMENTS

| | | |
|---|---|---|
| 2007/0254886 A1 | 11/2007 | Habashita et al. |
| 2012/0027723 A1 | 2/2012 | Picaud |

FOREIGN PATENT DOCUMENTS

| | | |
|---|---|---|
| JP | 2007-516938 A | 6/2007 |
| JP | 2015-096493 A | 5/2015 |
| WO | 97/10214 A1 | 3/1997 |
| WO | 2004/113277 A2 | 12/2004 |
| WO | 2005/023771 A1 | 3/2005 |

OTHER PUBLICATIONS

Guichou et al. Structure-based design, synthesis, and biological evaluation of novel inhibitors of human cyclophilin A. J. Med. Chem . 2006, 49, pp. 900-910.*
Igarashi, H. et al., "Water influx into cerebrospinal fluid is primarily controlled by aquaporin-4, not by aquaporin-1: 17-O JJVCPE MRI study in knockout mice," NeuroReport, vol. 25, No. 1, pp. 39-43, 2014.
Igarashi, H. et al., "Water influx into cerebrospinal fluid is significantly reduced in senile plaque bearing transgenic mice, supporting beta-amyloid clearance hypothesis of Alzheimer's disease," Neurol. Res., vol. 36, No. 12, pp. 1094-1098, 2014.
Suzuki, Y. et al., "Reduced CSF Water Influx in Alzheimer's Disease Supporting the β-Amyloid Clearance Hypothesis," PLOS One, DOI:10.1371/journal.pone.0123708, 2015.
Nakada T., et al., "Guanidinoethane sulfate: brain pH alkaline shifter," NeuroReport, vol. 4, No. 8, 1993.
Sakimura, et al. "Functional expression from cloned cDNAs of glutamate receptor species responsive to kainate and quisqualate," FEBS Lett. 272(1,2):73-80, 1990.
Igarashi, H. et al., "Guanidinoethane sulfate is neuroprotective towards delayed CA1 neuronal death in gerbils," Life Sciences. 56(14):1201-1206, 1995.
Huber V.J. et al., "Aquaporin-4 as a therapeutic target: a first look," Drugs of the Future, 33(10):897-909, 2008.

(Continued)

*Primary Examiner* — Jennifer M Kim
(74) *Attorney, Agent, or Firm* — Lathrop GPM LLP; Andrew T. Wilkins

(57) ABSTRACT

An aquaporin 4 function promotor contains a compound represented by Formula (1) or (2) or a pharmaceutically acceptable salt thereof, as an active ingredient.

$$NH_2C(NH)NH(CH_2)_{n11}SO_3H \quad (1)$$

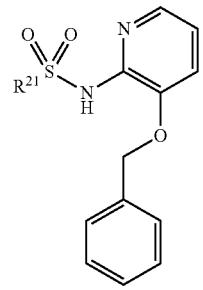

(2)

(In the formula, $n^{11}$ represents an integer of 1 to 10, and $R^{21}$ represents one selected from the group consisting of an alkyl group having 1 to 10 carbon atoms, an alicyclic heterocyclic group, an aromatic hydrocarbon group, and an aromatic heterocyclic group.)

3 Claims, 11 Drawing Sheets

Specification includes a Sequence Listing.

(56) References Cited

OTHER PUBLICATIONS

Chen W.Q. et al., "Role of taurine in regulation of intracellular calcium level and neuroprotective function in cultured neurons," Journal of Neuroscience Research 66(4):612-619, 2001.
Nakada T. et al., "Glymphatic fluid pharmacology: Facilitation of Beta-amyloid clearance., Alzheimer's and Dementia," 12(7), Supp. Supplement, p. P382-P383, Abstract No. O5-03-02, 2016.
International Search Report for PCT/JP2017/008485 dated Apr. 25, 2017. (Translation).

* cited by examiner

AQUAPORIN 4 FUNCTION PROMOTOR AND PHARMACEUTICAL COMPOSITION FOR NEUROLOGICAL DISORDERS

CROSS-REFERENCE TO RELATED APPLICATIONS

This application is a 35 U.S.C. § 371 filing of International Patent Application No. PCT/JP2017/008485, filed Mar. 3, 2017, which claims priority to Japanese Patent Application No. 2016-042766, filed Mar. 4, 2016, the entire contents of which are incorporated herein by reference.

TECHNICAL FIELD

The present invention relates to an aquaporin 4 function promotor and a pharmaceutical composition for neurological disorders.

Priority is claimed on Japanese Patent Application No. 2016-042766, filed on Mar. 4, 2016, the content of which is incorporated herein by reference.

BACKGROUND ART

Transport of water in and out of a cell in the brain is regulated by a transmembrane water channel which is referred to as the aquaporin family formed of an aquaporin (AQP) and an aquaglyceroporin. An aquaporin 4 (AQP 4) is one of the aquaporin families with extremely high water selectivity and is a main AQP associated with the transport of water in the brain. Further, a large amount of the AQP 4 is present in the brain, particularly in an end-feet membrane of astrocytes in contact with a basement membrane.

A perivascular space between blood vessels and brain tissues which are distributed in the brain is referred to as a "Virchow-Robin space" that is named after the discoverer. In recent years, it has been suggested that waste matter in protein decomposition products and other cells is transported through the Virchow-Robin space so as to be reabsorbed in the vena cava and flows into the cerebrospinal fluid (CSF) in the brain ventricle. This transporation is similar to a lymphatic system, and a system that discharges waste matter from the brain through the Virchow-Robin space is referred to as a glymphatic system.

It was found that the ability of discharging water into the brain ventricle through first and second perivascular spaces is weak in a case of mice in which the AQP 4 is genetically deleted and the glymphatic system is dependent on the expression level of the AQP 4 (for example, see Non-Patent Document 1).

Further, amyloid β protein (Aβ) serving as a main constituent component of senile plaques which are one of the pathological features of Alzheimer's disease and a by-product produced when cutting the amyloid β protein are known to be discharged through the glymphatic system. It was suggested that the ability of discharging water into the brain ventricle through first and second perivascular spaces is weak in a case of Alzheimer's disease model gene-modified mice and Aβ is accumulated (for example, see Non-Patent Document 2).

In addition, it was suggested that the flow of waste matter from the perivascular space into the CSF is significantly decreased in the brains of the Alzheimer's disease patients (for example, see Non-Patent Document 3).

Accordingly, it can be expected to delay the onset and progression of Alzheimer's disease by promoting transport of water using the AQP 4 in the brain so that the flow of the CSF that weakens with age and the discharge function using the glymphatic system are promoted.

Patent Document 1 describes an aquaporin function enhancer containing hyaluronic acid as an active ingredient used for the purpose of enhancing mainly the function of the AQP 2 or AQP 3.

CITATION LIST

Patent Literature

[Patent Document 1] Japanese Unexamined Patent Application, First Publication No. 2015-96493

Non-Patent Literature

[Non-Patent Document 1] Igarashi, H. et al., "Water influx into cerebrospinal fluid is primarily controlled by aquaporin-4, not by aquaporin-1: 17O JJVCPE MRI study in knockout mice", NeuroReport, Vol. 25, No. 1, p. 39 to 43, 2014.

[Non-Patent Document 2] Igarashi, H. et al., "Water influx into cerebrospinal fluid is significantly reduced in senile plaque bearing transgenic mice, supporting beta-amyloid clearance hypothesis of Alzheimer's disease", Neurol. Res., Vol. 36, No. 12, p. 1094 to 1098, 2014.

[Non-Patent Document 3] Suzuki, Y. et al., "Reduced CSF Water Influx in Alzheimer's Disease Supporting the β-Amyloid Clearance Hypothesis", PLOS ONE, DOI: 10.1371/journal.pone.0123708, 2015.

SUMMARY OF INVENTION

Technical Problem

The aquaporin function enhancer described in Patent Document 1 targets mainly the AQP 2 or AQP 3, and it has not been verified whether this aquaporin function enhancer promotes the function of the AQP 4.

The present invention has been made in consideration of the above-described circumstances, and an object thereof is to provide a novel aquaporin 4 function promotor which has an action of directly promoting the function of the AQP 4 and is useful for treating disorders.

Solution to Problem

The present invention includes the following aspects.

According to a first aspect of the present invention, there is provided an aquaporin 4 function promotor containing: a compound represented by Formula (1) or a pharmaceutically acceptable salt thereof, as an active ingredient.

$$NH_2C(NH)NH(CH_2)_{n11}SO_3H \qquad (1)$$

(In the formula, $n^{11}$ represents an integer of 1 to 10.)

The compound may be 2-guanidino-1-ethanesulfonic acid.

According to a second aspect of the present invention, there is provided a pharmaceutical composition for neurological disorders containing: the aquaporin 4 function promotor according to the first aspect; and at least any of a pharmaceutically acceptable carrier and a pharmaceutically acceptable diluent.

The neurological disorder may be any one selected from the group consisting of Alzheimer's disease, a cerebral infarction, and a brain tumor.

According to a third aspect of the present invention, there is provided an aquaporin 4 function promotor containing: a compound represented by Formula (2) or a pharmaceutically acceptable salt thereof, as an active ingredient.

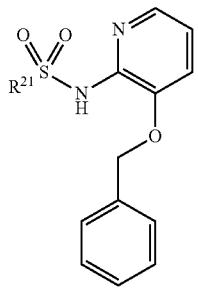

(2)

(In the formula, $R^{21}$ represents an alkyl group having 1 to 10 carbon atoms, an alicyclic heterocyclic group, an aromatic hydrocarbon group, or an aromatic heterocyclic group.)

$R^{21}$ may represent one selected from the group consisting of a methyl group, an ethyl group, an n-propyl group, an i-propyl group, an n-butyl group, an i-butyl group, a sec-butyl group, an n-pentyl group, an i-pentyl group, an n-hexyl group, a cyclopropyl group, a cyclobutyl group, a cyclopentyl group, a cyclohexyl group, a 2-pyrrolidinyl group, a 3-pyrrolidinyl group, a 2-tetrahydrofuranyl group, a 3-tetrahydrofuranyl group, a 2-pyrrolyl group, a 3-pyrrolyl group, a 2-furanyl group, or a 3-furanyl group.

The compound may be 2-phenylsulfoamido-3-benzyloxy-pyrimidine.

According to a fourth aspect of the present invention, there is provided a pharmaceutical composition for neurological disorders containing: the aquaporin 4 function promotor according to the third aspect; and at least any of a pharmaceutically acceptable carrier and a pharmaceutically acceptable diluent.

The neurological disorder may be any one selected from the group consisting of Alzheimer's disease, a cerebral infarction, and a brain tumor.

Advantageous Effects of Invention

According to the above-described aspects, it is possible to provide a novel aquaporin 4 function promotor which has an action of directly promoting the function of the AQP 4 and is useful for treating diseases.

DESCRIPTION OF EMBODIMENTS

Aquaporin 4 Function Promotor

First Embodiment

Figure 1:
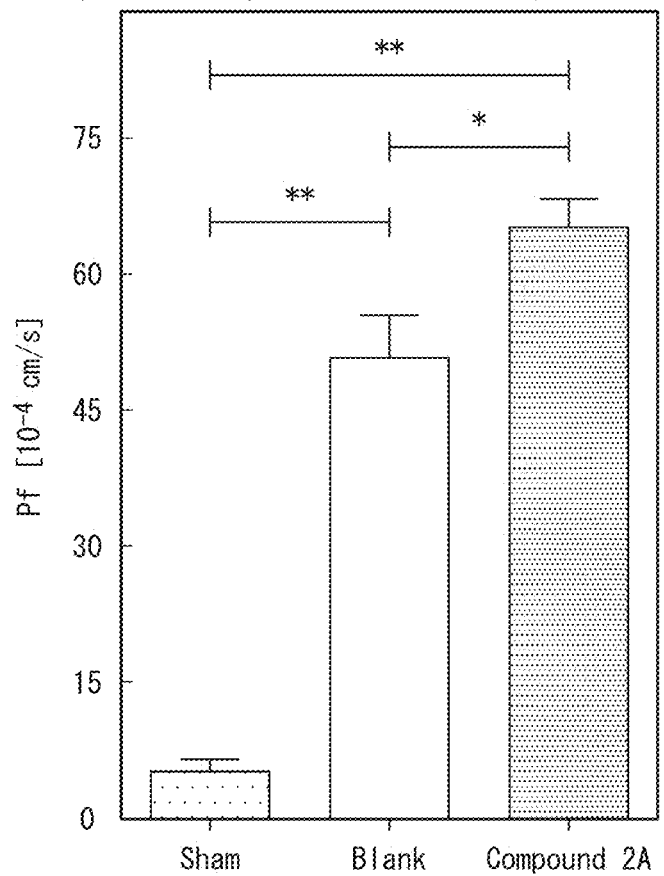
FIG. 1 is a graph showing the results of an in vitro assay using the oocytes of a *Xenopus laevis* for evaluating an AQP 4 function promotor candidate compound in Example 1.

An aquaporin 4 (AQP 4) function promotor according to a first embodiment of the present invention contains a compound represented by Formula (1) (in the present specification, also referred to as a "compound (1)") or a pharmaceutically acceptable salt thereof, as an active ingredient.

$$NH_2C(NH)NH(CH_2)_{n11}SO_3H \quad (1)$$

(In the formula, $n^{11}$ represents an integer of 1 to 10.)

The AQP 4 function promotor of the present embodiment has an action of directly promoting the function of the AQP 4 and can be used for treating mainly neurological disorders.

The present inventors clarified that 2-guanidino-1-ethane-sulfonic acid (guanidinoethyl sulfonate; GES) serves as an alkaline shifter for the brain pH (reference: Nakada T., et al., "Guanidinoethane sulfate: brain pH alkaline shifter", Neurochemistry, vol. 4, no. 8, 1993). As described in the following examples, it was found that GES and the compound (1) which is the analogue thereof have an excellent AQP 4 function promoting effect based on the test carried out using Alzheimer's disease model mice.

In the present specification, the "promotion of the function of the AQP 4" means that the transport of water through the AQP 4 is promoted. By promoting the transport of water through the AQP 4, the flow of the CSF and discharge function using a glymphatic system are promoted so that disorders caused by degradation of these functions can be prevented or treated.

Examples of the disorders which can be prevented or treated using the AQP 4 function promotor of the present embodiment include mainly neurological disorders, and specific examples thereof include cerebral edema, cerebral ischemia, a cerebral infarction, a brain tumor, a demyelinating disease, epilepsy, neuropathic pain, a migraine, bipolar disorder, major depressive disorder, schizophrenia, Parkinson's disease, Alzheimer's disease, and complications caused by these disorders.

[Compound (1)]

The compound (1) is a compound containing a guanidino group and a sulfo group and is directly bonded to the APQ 4.

($n^{11}$)

$n^{11}$ represents an integer of 1 to 10. $n^{11}$ represents a repetition number of alkylene groups. From the viewpoint of high hydrophilicity, $n^{11}$ represents preferably an integer of 1 to 8, more preferably an integer of 1 to 6, still more preferably an integer of 1 to 4, and particularly preferably an integer of 1 or 2.

Preferred examples of the compound (1) include the following compounds.

Further, these compounds are merely preferred examples of the compound (1) and the preferred examples of the compound (1) are not limited thereto.

NH$_2$C(NH)NHCH$_2$SO$_3$H

NH$_2$C(NH)NH(CH$_2$)$_2$SO$_3$H

NH$_2$C(NH)NH(CH$_2$)$_3$SO$_3$H

NH$_2$C(NH)NH(CH$_2$)$_4$SO$_3$H

Among these, it is preferable that the compound (1) is NH$_2$C(NH)NH(CH$_2$)$_2$SO$_3$H, that is, 2-guanidino-1-ethanesulfonic acid (guanidinoethyl sulfonate; GES). GES is a known compound, and various clinical studies have been performed already. Further, GES is suitable from the viewpoint of the safety.

The AQP 4 function promotor of the present embodiment may contain a pharmaceutically acceptable salt of the compound (1).

In the present specification, the term "pharmaceutically acceptable" generally means the extent that side effects do not occur in a case where the promotor is appropriately administered to a test animal.

As the salt, a pharmaceutically acceptable acid addition salt or basic salt is preferable. Examples of the acid addition salt include a salt with an inorganic acid such as hydrochloric acid, phosphoric acid, hydrobromic acid, or sulfuric acid; and a salt with an organic acid such as acetic acid, formic acid, propionic acid, fumaric acid, maleic acid, succinic acid, tartaric acid, citric acid, malic acid, benzoic acid, methanesulfonic acid, or benzenesulfonic acid.

Examples of the basic salt include a salt with an inorganic base such as sodium hydroxide, potassium hydroxide, ammonium hydroxide, or magnesium hydroxide; and a salt with an organic base such as caffeine, piperidine, trimethylamine, or pyridine.

The AQP 4 function promotor of the present embodiment may contain a buffer solution such as PBS or Tris-HCl, and an additive such as sodium azide or glycerol, as other components.

A method of treating disorders (particularly, neurological disorders) can be provided using the AQP 4 function promotor of the present embodiment.

A treatment target is not limited, and examples thereof include humans and mammals other than humans. Among these, humans are preferable.

[Method of Producing Compound (1)]

The compound (1) can be produced by reacting, for example, sodium sulfite, a halide having desired $R^{11}$, and aliphatic hydrocarbon containing a guanidino group, using a known reaction. The method will be described in more detail below.

The compound (1) can be produced according to a production method including the following two steps.

First step (hereinafter, also abbreviated as a "step of producing the compound (1)"): reacting a compound represented by Formula (1a) (hereinafter, also abbreviated as a "compound (1a)") with sodium sulfite to obtain a compound represented by Formula (1b) (hereinafter, also abbreviated as a "compound (1b)")

Second step (hereinafter, also abbreviated as a "step of producing the compound (1)"): reacting the compound (1b) with a compound represented by Formula (1c) (hereinafter, also abbreviated as a "compound (1c)") to obtain the compound (1)

Hereinafter, each step will be described in detail.

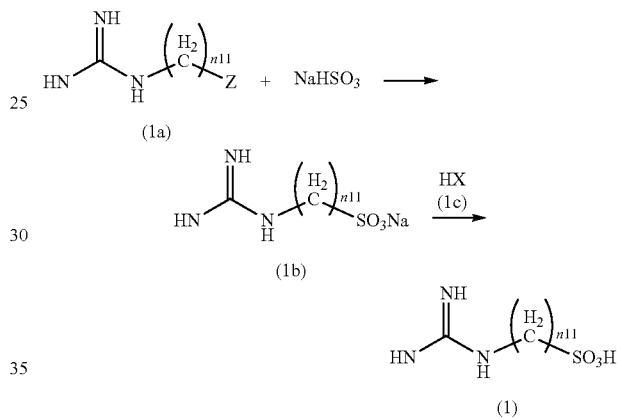

(In the formula, X represents a halogen atom, Z represents a halogen atom or a leaving group (such as a methanesulfonyloxy group or a p-toluenesulfonyloxy group), and $n^{11}$ has the same definition as described above.)

[Step of Producing Compound (1b)]

In the step of producing the compound (1b), the compound (1) is obtained by reacting the compound (1a) with sodium sulfite.

(Compound (1a))

The compound (1a) is a known compound.

In the compound (1a), $n^{11}$ represents an integer of 1 to 10. $n^{11}$ represents a repetition number of alkylene groups. From the viewpoint of high hydrophilicity, $n^{11}$ represents preferably an integer of 1 to 8, more preferably an integer of 1 to 6, still more preferably an integer of 1 to 4, and particularly preferably an integer of 1 or 2.

(Compound (1b))

The compound (1b) is a known compound.

In the compound (1b), $n^{11}$ has the same definition as that for $n^{11}$ in the compound (1a).

(Conditions for Reaction)

In the step of producing the compound (1b), for example, it is preferable to appropriately use an aqueous solvent such as an organic solvent or a mixed solvent of the organic solvent and water as a reaction solvent.

Examples of the organic solvent which can be used in the step of producing the compound (1b) include methanol, ethanol, acetone, dichloromethane, chloroform, toluene, trifluoromethylbenzene, dimethylsulfoxide, N,N-dimethylformamide, tetrahydrofuran, tetrahydropyran, 1,4-dioxane, and methyl-tert-butyl ether, and the present invention is not limited thereto.

The solvent may be used alone or in combination of two or more kinds thereof. In a case where two or more solvents are used in combination, the combinations and the proportions of the solvents can be optionally selected.

In the step of producing the compound (1b), the amount of sodium sulfite to be used is preferably in a range of 0.5 to 2 times the molar amount of the compound (1a) and more preferably in a range of to 1.5 times the molar amount of the compound (1a).

In the step of producing the compound (1b), it is preferable that the reaction is further performed using an additive.

Examples of the additive include sodium iodide, but the present invention is not limited thereto.

In the step of producing the compound (1b), the amount of the additive to be used is preferably in a range of 0.1 to 1 time the molar amount of the compound (1a) and more preferably in a range of 0.2 to 0.5 times the molar amount of the compound (1a).

In the step of producing the compound (1b), the reaction temperature is, for example, preferably in a range of 15° C. to 40° C. and more preferably in a range of 20° C. to 30° C.

In the step of producing the compound (1b), the reaction time is, for example, preferably in a range of 48 to 96 hours and more preferably in a range of 60 to 84 hours.

In the step of producing the compound (1b), the compound (1b) may be taken out by performing a post-treatment as necessary using a known technique after the reaction is completed. In other words, the compound (1b) may be taken out through concentration, crystallization, re-precipitation, column chromatography, or the like by appropriately performing any one or two or more post-treatment operations from among filtration, washing, extraction, pH adjustment, dehydration, concentration, and the like as necessary. Further, the taken-out compound (1b) may be purified by performing any one or two or more operations from among crystallization, re-precipitation, column chromatography, extraction, stirring and washing of crystals using a solvent, and the like as necessary at least once.

In the step of producing the compound (1b), the next step may be performed without taking the compound (1b) out after the reaction is completed, but it is preferable that the compound (1b) is taken out according to the above-described method from the viewpoint of improving the yield coefficient of the compound (1) serving as a target object.

[Step of Producing Compound (1)]

In the step of producing the compound (1), the compound (1) is obtained by reacting the compound (1b) with the compound (1c).

The reaction from which the compound (1) is obtained is a known substitution reaction.

(Compound (1c))

The compound (1c) is known hydrogen halide. Specific examples thereof include HF, HCl, HBr, and HI, but the present invention is not limited thereto.

(Conditions for Reaction)

In the step of producing the compound (1), for example, it is preferable to appropriately use an aqueous solvent such as an organic solvent or a mixed solvent of the organic solvent and water as a reaction solvent.

Examples of the organic solvent which can be used in the step of producing the compound (1) are the same as those exemplary examples in the section regarding the [Step of producing compound (1b)].

The solvent may be used alone or in combination of two or more kinds thereof. In a case where two or more solvents are used in combination, the combinations and the proportions of the solvents can be optionally selected.

In the step of producing the compound (1), the amount of the compound (1c) to be used is preferably in a range of 0.5 to 2 times the molar amount of the compound (1b) and more preferably in a range of 1 to 1.5 times the molar amount of the compound (1b).

In the step of producing the compound (1), it is preferable that the reaction is further performed using an acid.

Examples of the acid include an inorganic acid such as hydrochloric acid; and an organic acid such as acetic acid or paratoluenesulfonic acid.

The acid may be used alone or in combination of two or more kinds thereof. In a case where two or more acids are used in combination, the combinations and the proportions of the acids can be optionally selected.

In the step of producing the compound (2), the amount of the acid to be used is preferably in a range of 1 to 5 times the molar amount of the compound (1b) and more preferably in a range of 2 to 4 times the molar amount of the compound (1b).

In the step of producing the compound (1), the reaction temperature is, for example, preferably in a range of 15° C. to 40° C. and more preferably in a range of 20° C. to 30° C.

In the step of producing the compound (1), the reaction time is, for example, preferably in a range of 48 to 96 hours and more preferably in a range of 60 to 84 hours.

In the step of producing the compound (1), the compound (1) may be taken out by performing a post-treatment as necessary using a known technique after the reaction is completed. In other words, the compound (1) may be taken out through concentration, crystallization, re-precipitation, column chromatography, or the like by appropriately performing any one or two or more post-treatment operations from among filtration, washing, extraction, pH adjustment, dehydration, concentration, and the like as necessary. Further, the taken-out compound (1) may be purified by performing any one or two or more operations from among crystallization, re-precipitation, column chromatography, extraction, stirring and washing of crystals using a solvent, and the like as necessary at least once.

The structure of each compound such as the compound (1), the compound (1a), the compound (1b), or the compound (1c) can be verified according to a known technique such as nuclear magnetic resonance (NMR) spectroscopy, mass spectrometry (MS), or infrared spectroscopy (IR).

Second Embodiment

An aquaporin 4 (AQP 4) function promotor according to a second embodiment of the present invention contains a compound represented by Formula (2) (in the present specification, also referred to as a "compound (2)") or a pharmaceutically acceptable salt thereof, as an active ingredient.

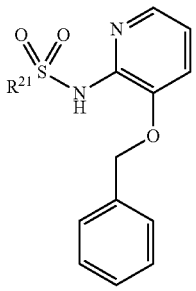

(2)

(In the formula, $R^{21}$ represents an alkyl group having 1 to 10 carbon atoms, an alicyclic heterocyclic group, an aromatic hydrocarbon group, or an aromatic heterocyclic group.)

The AQP 4 function promotor of the present embodiment has an action of directly promoting the function of the AQP 4 and can be used for treating mainly neurological disorders.

The present inventors searched AQP 4 function promotor candidates from the low molecular weight compound library using in silico screening which is a computer simulation. Further, as described in the following examples, a compound is selected based on the ability of increasing the volume under a hyposmotic condition of 60 to 80 mOsm in the oocytes of a *Xenopus laevis* obtained by transfecting AQP 4 mRNA so as to express the AQP 4. Based on the obtained results, it was found that the compound (2) has an excellent AQP 4 function promoting effect.

[Compound (2)]

The compound (2) is a compound having a 2-sulfonamido-3-benzyloxypyridine skeleton and is directly bonded to the AQP 4.

($R^{21}$)

In Formula (2), $R^{21}$ represents an alkyl group having 1 to 10 carbon atoms, an alicyclic heterocyclic group, an aromatic hydrocarbon group, or an aromatic heterocyclic group.

The alkyl group having 1 to 10 carbon atoms as $R^{21}$ may be linear, branched, or cyclic. In a case of being cyclic, the alkyl group may be monocyclic or polycyclic. In addition, the number of carbon atoms of the alkyl group is preferably in a range of 1 to 10, more preferably in a range of 1 to 8, still more preferably in a range of 1 to 6, and particularly preferably in a range of 1 to 4.

Examples of the linear or branched alkyl group include a methyl group, an ethyl group, an n-propyl group, an isopropyl group, an n-butyl group, an isobutyl group, a sec-butyl group, a tert-butyl group, an n-pentyl group, an isopentyl group, an neopentyl group, a tert-pentyl group, a 1-methylbutyl group, an n-hexyl group, a 2-methylpentyl group, a 3-methylpentyl group, a 2,2-dimethylbutyl group, a 2,3-dimethylbutyl group, an n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, an n-octyl group, an isooctyl group, a 2-ethylhexyl group, a nonyl group, and a decyl group.

The number of carbon atoms of the linear or branched alkyl group is preferably in a range of 1 to 10, more preferably in a range of 1 to 8, still more preferably in a range of 1 to 6, and particularly preferably in a range of 1 to 4.

More specifically, it is preferable that the linear or branched alkyl group as $R^{21}$ is a methyl group, an ethyl group, an n-propyl group, an i-propyl group, an n-butyl group, an i-butyl group, a sec-butyl group, an n-pentyl group, an i-pentyl group, or an n-hexyl group.

Examples of the cyclic alkyl group include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, a 2-adamantyl group, and a tricyclodecyl group, and other examples thereof include those obtained by substituting one or more hydrogen atoms in these cyclic alkyl groups with halogen atoms, hydroxyl groups, or linear, branched, or cyclic alkyl groups. Here, examples of the halogen atoms substituting hydrogen atoms include a fluorine atom, a chlorine atom, a bromine atom, and an iodine atom. Further, examples of the linear, branched, or cyclic alkyl group include those described as examples of the alkyl group as $R^{21}$.

It is preferable that the cyclic alkyl group is monocyclic. Further, the number of carbon atoms in the cyclic alkyl group is preferably in a range of 3 to 10, more preferably in a range of 3 to 8, and still more preferably in a range of 3 to 6.

More specifically, it is preferable that the cyclic alkyl group as $R^{21}$ is a cyclopropyl group, a cyclobutyl group, a cyclopentyl group, or a cyclohexyl group.

The alicyclic heterocyclic group as $R^{21}$ is formed of carbon and other elements (for example, nitrogen, oxygen, and sulfur). The alicyclic heterocyclic group may be monocyclic or polycyclic.

Examples of the alicyclic heterocyclic group include a nitrogen-containing alicyclic heterocyclic group such as an ethyleneimino group, an azacyclobutyl group, a pyrrolidinyl group, a piperidyl group, a piperidino group, a piperazinyl group, a hexamethyleneimino group, a heptamethyleneimino group, an octamethyleneimino group, a nonamethyleneimino group, or a 1,3,5,7-tetraazaadamantyl group; an oxygen-containing alicyclic heterocyclic group such as an epoxy group, a trimethylene oxide group, a tetrahydrofuranyl group, a tetrahydropyranyl group, a hexamethylene oxide group, a heptamethylene oxide group, an octamethylene oxide group, a nonamethylene oxide group, or a 2,4,6,8,9,10-hexaoxaadamantyl group; a sulfur-containing alicyclic heterocyclic group such as an ethylene sulfide group, a trimethylene sulfide group, a tetrahydrothienyl group, a tetrahydrothiopyranyl group, a hexamethylene sulfide group, a heptamethylene sulfide group, an octamethylene sulfide group, a nonamethylene sulfide group, or a 2,4,6,8,9,10-hexathiaadamantyl group; a nitrogen and oxygen-containing alicyclic heterocyclic group such as a morpholino group; and a nitrogen and sulfur-containing alicyclic heterocyclic group such as a thiomorpholino group, and other examples thereof include those obtained by substituting one or more hydrogen atoms in these cyclic alkyl groups with halogen atoms, hydroxyl groups, or linear, branched, or cyclic alkyl groups. Here, examples of the halogen atoms substituting hydrogen atoms include a fluorine atom, a chlorine atom, a bromine atom, and an iodine atom. Further, examples of the linear, branched, or cyclic alkyl group include those exemplified in ($R^{11}$).

It is preferable that the alicyclic heterocyclic group is monocyclic. Further, the number of atoms constituting a ring in the alicyclic heterocyclic group is preferably in a range of 3 to 10, more preferably in a range of 3 to 8, and still more preferably in a range of 3 to 6.

More specifically, it is preferable that the alicyclic heterocyclic group as $R^{21}$ is a 2-pyrrolidinyl group, a 3-pyrrolidinyl group, a 2-tetrahydrofuranyl group, or a 3-tetrahydrofuranyl group.

The aromatic hydrocarbon group as $R^{21}$ may be monocyclic or polycyclic.

Examples of the aromatic hydrocarbon group include a phenyl group, a pentalenyl group, an indenyl group, a naphthyl group, an anthracenyl group, an azulenyl group, a heptalenyl group, and an octalenyl group, and other examples thereof include those obtained by substituting one or more hydrogen atoms in these aromatic hydrocarbon groups with halogen atoms, hydroxyl groups, or linear, branched, or cyclic alkyl groups. Here, examples of the halogen atoms substituting hydrogen atoms include a fluorine atom, a chlorine atom, a bromine atom, and an iodine atom. Further, examples of the linear, branched, or cyclic alkyl group include those exemplified in ($R^{11}$).

It is preferable that the aromatic hydrocarbon group is monocyclic. Further, the number of carbon atoms in the aromatic hydrocarbon group is preferably in a range of 6 to 14, more preferably in a range of 6 to 12, and still more preferably in a range of 6 to 10.

More specifically, it is preferable that the aromatic hydrocarbon group as $R^{21}$ is a phenyl group, a 2-methylphenyl group, a 3-methylphenyl group, a 4-methylphenyl group, a 2,3-dimethylphenyl group, a 3,4-dimethylphenyl group, a 2,4-dimethylphenyl group, a 2,4,6-trimethylphenyl group, a 2-fluorophenyl group, a 3-fluorophenyl group, a 4-fluorophenyl group, a 2,4-difluorophenyl group, a 3,5-difluorophenyl group, a 2-(trifluoromethyl)phenyl group, a 3-(trifluoromethyl)phenyl group, or a 4-(trifluoromethyl)phenyl group.

The aromatic heterocyclic group as $R^{21}$ is formed of carbon and other elements (for example, nitrogen, oxygen, and sulfur). The aromatic heterocyclic group may be monocyclic or polycyclic.

Examples of the aromatic heterocyclic group include a nitrogen-containing aromatic heterocyclic group such as a pyrrolyl group, an imidazolyl group, a pyrazolyl group, a pyrazyl group, a pyridyl group, a pyrazinyl group, a pyrimidinyl group, a pyridazinyl group, an indolizinyl group, an indolyl group, an isoindolyl group, an indazolyl group, a purinyl group, a quinozinyl group, a quinolyl group, an isoquinolyl group, a naphthyridinyl group, a phthalazinyl group, a quinoxalinyl group, a quinazolinyl group, a cinnolinyl group, a pteridinyl group, a carbazolyl group, a 3-carbolinyl group, a phenanthridinyl group, an acridinyl group, a perimidinyl group, a phenanthrolinyl group, a phenazinyl group, or an anthyridinyl group; an oxygen-containing aromatic heterocyclic group such as a furanyl group (furyl group), a pyranyl group, a benzofuranyl group, an isobenzofuranyl group, a chromenyl group, an isochromenyl group, or a xanthenyl group; a sulfur-containing aromatic heterocyclic group such as a thienyl group, a thiopyranyl group, a thiochromenyl group, an isothiochromenyl group, a thioxanthenyl group, an isothioxanthenyl group, or a thianthrenyl group; a nitrogen and oxygen-containing aromatic heterocyclic group such as an oxazolyl group, an isoxazolyl group, a furazanyl group, or a phenoxazinyl group; a nitrogen and sulfur-containing aromatic heterocyclic group such as a thiazolyl group, an isothiazolyl group, or a phenothiazinyl group; and an oxygen and a sulfur-containing aromatic heterocyclic group such as a phenoxathiinyl group, and other examples thereof include those obtained by substituting one or more hydrogen atoms in these aromatic heterocyclic groups with halogen atoms, hydroxyl groups, or linear, branched, or cyclic alkyl groups. Here, examples of the halogen atoms substituting hydrogen atoms include a fluorine atom, a chlorine atom, a bromine atom, and an iodine atom. Further, examples of the linear, branched, or cyclic alkyl group include those exemplified in ($R^{11}$).

It is preferable that the aromatic heterocyclic group is monocyclic. Further, the number of carbon atoms in the aromatic heterocyclic group is preferably in a range of 5 to 14, more preferably in a range of 5 to 12, and still more preferably in a range of 5 to 10.

More specifically, it is preferable that the aromatic heterocyclic group as $R^{21}$ is a 2-pyrrolyl group, a 3-pyrrolyl group, a 2-furanyl group, or a 3-furanyl group.

Among these, it is preferable that $R^{21}$ in the compound (2) represents a methyl group, an ethyl group, an n-propyl group, an i-propyl group, an n-butyl group, an i-butyl group, a sec-butyl group, an n-pentyl group, an i-pentyl group, an n-hexyl group, a cyclopropyl group, a cyclobutyl group, a cyclopentyl group, a cyclohexyl group, a 2-pyrrolidinyl group, a 3-pyrrolidinyl group, a 2-tetrahydrofuranyl group, a 3-tetrahydrofuranyl group, a 2-pyrrolyl group, a 3-pyrrolyl group, a 2-furanyl group, or a 3-furanyl group.

Preferred examples of the compound (2) include the following compounds in a case where $R^{21}$ represents an alkyl group having 1 to 10 carbon atoms. Further, these compounds are merely preferred examples of the compound (2) and the preferred examples of the compound (2) are not limited thereto.

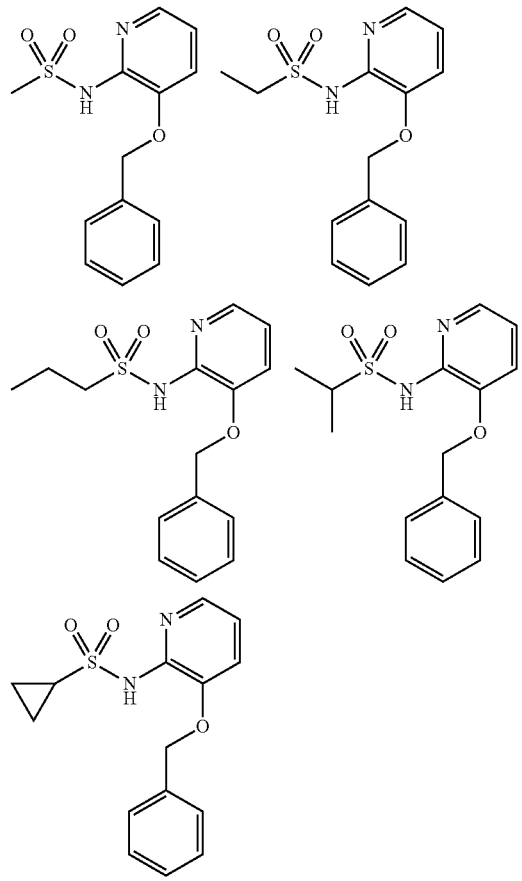

-continued
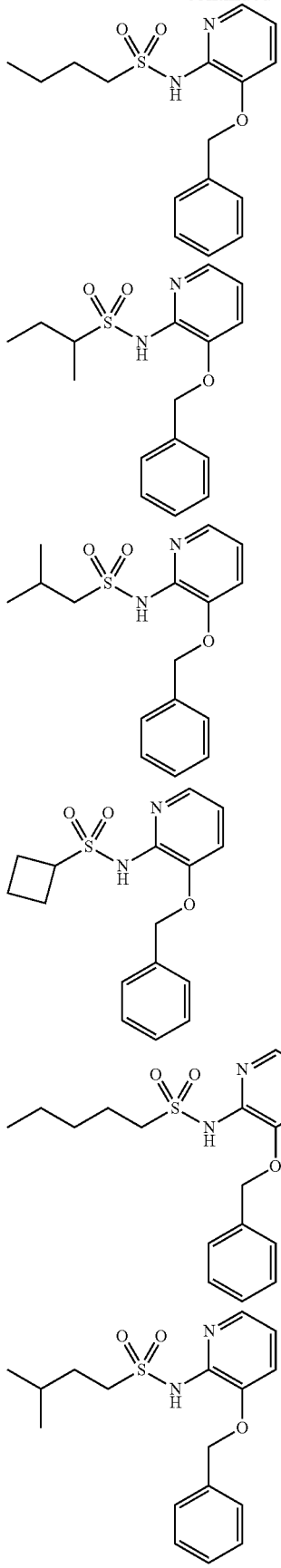
-continued
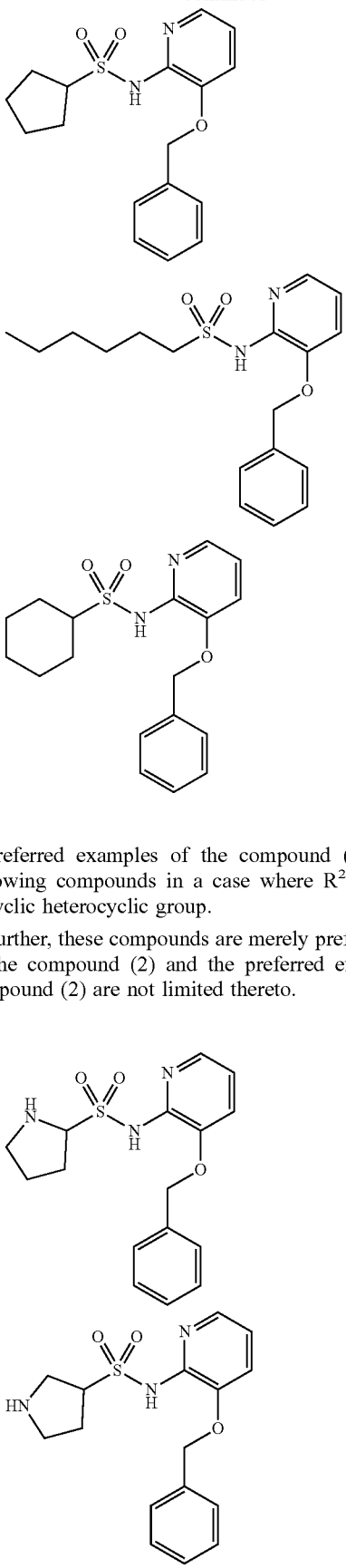
Preferred examples of the compound (2) include the following compounds in a case where $R^{21}$ represents an alicyclic heterocyclic group.
Further, these compounds are merely preferred examples of the compound (2) and the preferred examples of the compound (2) are not limited thereto.

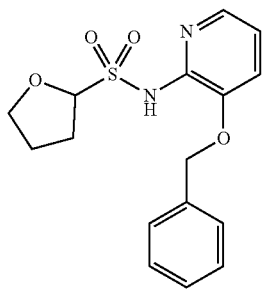
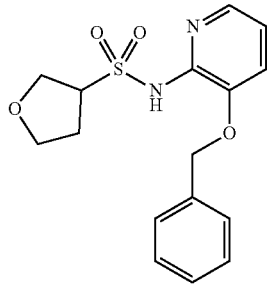
Preferred examples of the compound (2) include the following compounds in a case where $R^{21}$ represents an aromatic hydrocarbon group.
Further, these compounds are merely preferred examples of the compound (2) and the preferred examples of the compound (2) are not limited thereto.
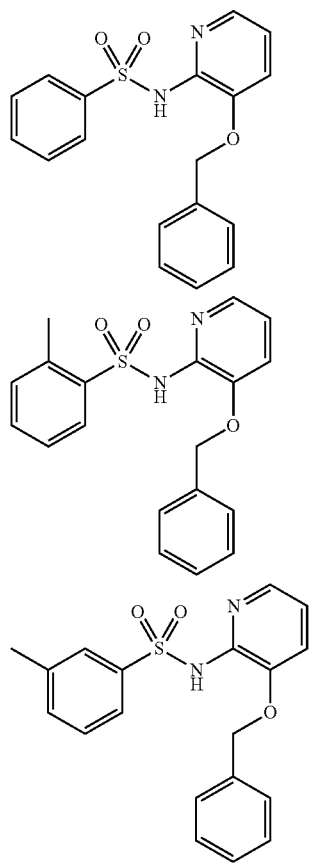
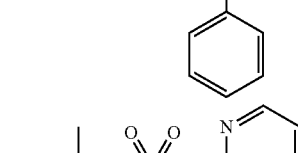
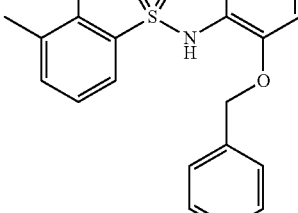
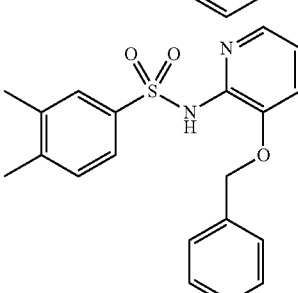
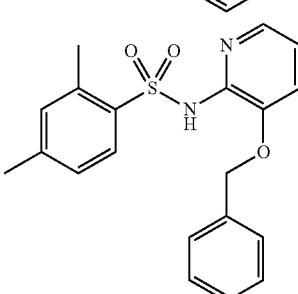
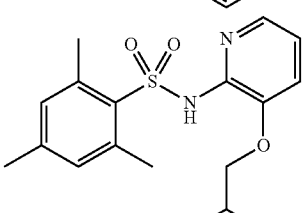

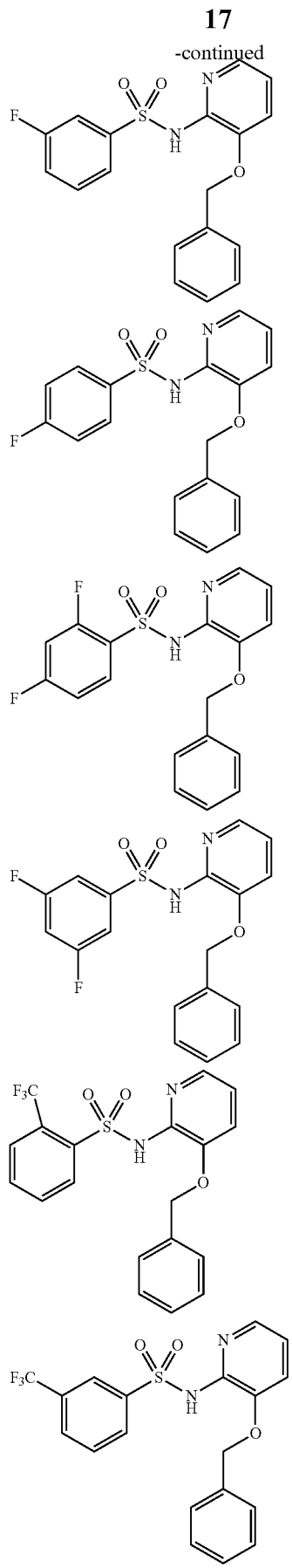
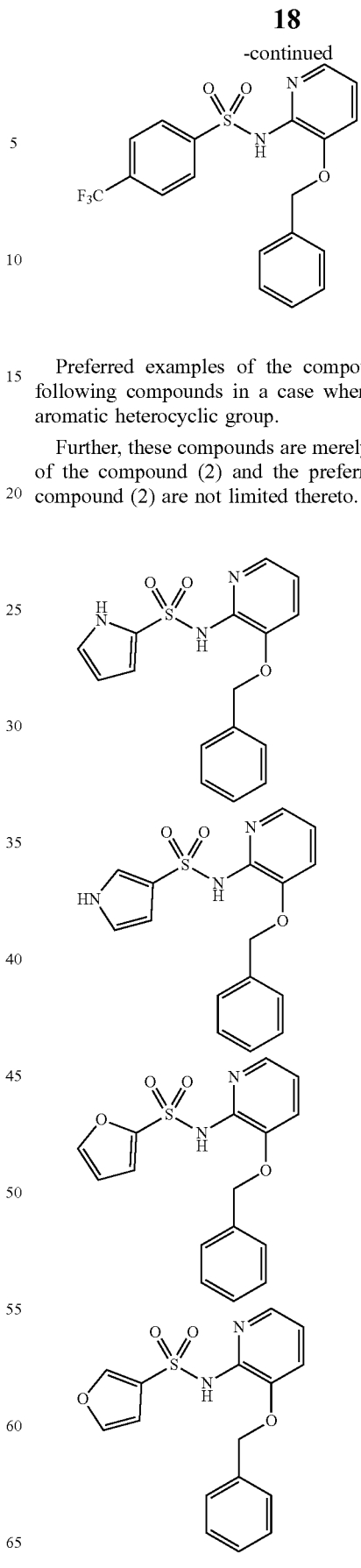
Preferred examples of the compound (2) include the following compounds in a case where $R^{21}$ represents an aromatic heterocyclic group.
Further, these compounds are merely preferred examples of the compound (2) and the preferred examples of the compound (2) are not limited thereto.

Among the examples, as described in the following example, from the viewpoint of having an excellent AQP 4 function promoting effect, it is preferable that the compound (2) is a 2-phenylsulfoamido-3-benzyloxypyrimidine.

The AQP 4 function promotor of the present embodiment may contain a pharmaceutically acceptable salt of the compound (2).

The AQP 4 function promotor of the present embodiment may contain a buffer solution such as PBS or Tris-HCl, and an additive such as sodium azide or glycerol, as other components.

A method of treating disorders (particularly, neurological disorders) can be provided using the AQP 4 function promotor of the present embodiment.

A treatment target is not limited, and examples thereof include humans and mammals other than humans. Among these, humans are preferable.

[Method of Producing Compound (2)]

The compound (2) can be produced by condensing, for example, sulfonyl chloride having desired $R^{21}$ and 2-amino-3-benzyloxypyridine using a known reaction. The method will be described in more detail below.

The compound (2) can be produced according to a production method including a step of reacting a compound represented by Formula (2a) (hereinafter, also abbreviated as a "compound (2a)") with a compound represented by Formula (2b) (hereinafter, also abbreviated as a "compound (2b)") to obtain the compound (2) (hereinafter, also abbreviated as a "step of producing the compound (2)").

Hereinafter, each step will be described in detail.

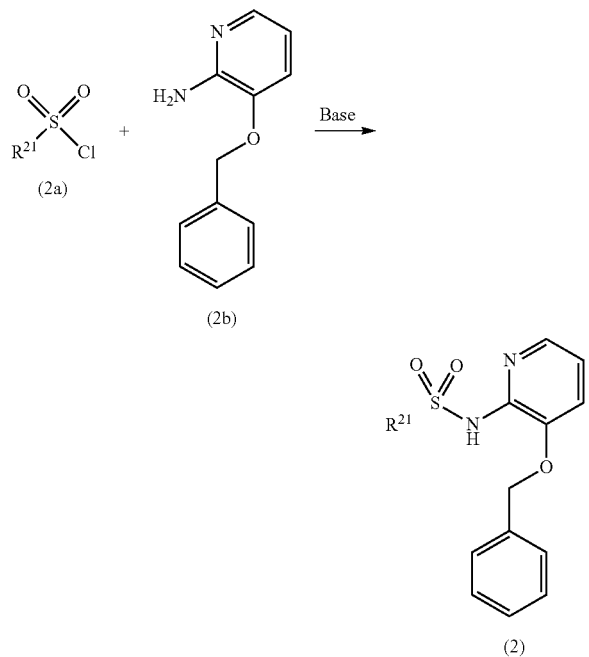

(In the formula, $R^{21}$ has the same definition as described above.)

[Step of Producing Compound (2)]

In the step of producing the compound (2), the compound (2) is obtained by reacting the compound (2a) with the compound (2b).

The reaction from which the compound (2) is obtained is a known condensation reaction.

(Compound (2a))

The compound (2a) is a known compound.

In the compound (2a), in a case where $R^{21}$ represents a linear or branched alkyl group having 1 to 10 carbon atoms, it is preferable that the alkyl group is a methyl group, an ethyl group, an n-propyl group, an i-propyl group, an n-butyl group, an i-butyl group, a sec-butyl group, an n-pentyl group, an i-pentyl group, or an n-hexyl group.

In a case where $R^{21}$ represents a cyclic alkyl group having 1 to 10 carbon atoms, it is preferable that the alkyl group is a cyclopropyl group, a cyclobutyl group, a cyclopentyl group, or a cyclohexyl group.

Further, in a case where $R^{21}$ represents an alicyclic heterocyclic group, it is preferable that the alicyclic heterocyclic group is a 2-pyrrolidinyl group, a 3-pyrrolidinyl group, a 2-tetrahydrofuranyl group, or a 3-tetrahydrofuranyl group.

Further, in a case where $R^{21}$ represents an aromatic hydrocarbon group, it is preferable that the aromatic hydrocarbon group is a phenyl group, a 2-methylphenyl group, a 3-methylphenyl group, a 4-methylphenyl group, a 2,3-dimethylphenyl group, a 3,4-dimethylphenyl group, a 2,4-dimethylphenyl group, a 2,4,6-trimethylphenyl group, a 2-fluorophenyl group, a 3-fluorophenyl group, a 4-fluorophenyl group, a 2,4-difluorophenyl group, a 3,5-difluorophenyl group, a 2-(trifluoromethyl)phenyl group, a 3-(trifluoromethyl)phenyl group, or a 4-(trifluoromethyl)phenyl group.

Further, in a case where $R^{21}$ represents an aromatic heterocyclic group, it is preferable that the aromatic heterocyclic group is a 2-pyrrolyl group, a 3-pyrrolyl group, a 2-furanyl group, or a 3-furanyl group.

(Compound (2b))

The compound (2b) is a known compound (2-amino-3-benzyloxypyridine). The compound (2b) may be synthesized using a known method. Alternatively, a commercially available product may be used as the compound.

(Conditions for Reaction)

In the step of producing the compound (2), for example, it is preferable to appropriately use an aqueous solvent such as an organic solvent or a mixed solvent of the organic solvent and water as a reaction solvent.

Examples of the organic solvent which can be used in the step of producing the compound (2) include dichloromethane, chloroform, toluene, trifluoromethylbenzene, tetrahydrofuran, tetrahydropyran, 1,4-dioxane, and methyl-tert-butyl ether, and the present invention is not limited thereto.

The solvent may be used alone or in combination of two or more kinds thereof. In a case where two or more solvents are used in combination, the combinations and the proportions of the solvents can be optionally selected.

In the step of producing the compound (2), the amount of the compound (2a) to be used is preferably in a range of 0.5 to 2 times the molar amount of the compound (2b) and more preferably in a range of 1 to 1.5 times the molar amount of the compound (2b).

In the step of producing the compound (2), it is preferable that the reaction is further performed using a base.

Examples of the base include an organic base such as pyridine, 2,6-lutidine, 2,6-bis(tert-butyl) pyridine, trimethylamine, dimethylisopropylamine, or N-methylmorpholine; an inorganic base such as sodium hydroxide, potassium hydroxide, sodium hydride, potassium hydride, or sodium amide; and an organic metal salt such as lithium diisopropylamide or butyl lithium, and the present invention is not limited thereto.

The base may be used alone or in combination of two or more kinds thereof. In a case where two or more bases are used in combination, the combinations and the proportions of the bases can be optionally selected.

In the step of producing the compound (2), the amount of the base to be used is preferably in a range of 1 to 5 times the molar amount of the compound (2b) and more preferably in a range of 2 to 4 times the molar amount of the compound (2b).

In the step of producing the compound (2), the reaction temperature is, for example, preferably in a range of 15° C. to 40° C. and more preferably in a range of 20° C. to 30° C.

In the step of producing the compound (2), the reaction time is, for example, preferably in a range of 48 to 96 hours and more preferably in a range of 60 to 84 hours.

In the step of producing the compound (2), it is preferable that the reaction is performed in an inert gas atmosphere.

Examples of the inert gas include argon gas, helium gas, and nitrogen gas.

In the step of producing the compound (2), the compound (2) may be taken out by performing a post-treatment as necessary using a known technique after the reaction is completed. In other words, the compound (2) may be taken out through concentration, crystallization, re-precipitation, column chromatography, or the like by appropriately performing any one or two or more post-treatment operations from among filtration, washing, extraction, pH adjustment, dehydration, concentration, and the like as necessary. Further, the taken-out compound (2) may be purified by performing any one or two or more operations from among crystallization, re-precipitation, column chromatography, extraction, stirring and washing of crystals using a solvent, and the like as necessary at least once.

The structure of each compound such as the compound (2), the compound (2a), or the compound (2b) can be verified according to a known technique such as nuclear magnetic resonance (NMR) spectroscopy, mass spectrometry (MS), or infrared spectroscopy (IR).

<<Pharmaceutical Composition for Neurological Disorders>>

The pharmaceutical composition for neurological disorders according to the embodiment of the present invention contains the above-described aquaporin 4 function promotor, and at least any of a pharmaceutically acceptable carrier and a pharmaceutically acceptable diluent.

According to the pharmaceutical composition for neurological disorders of the present embodiment, neurological disorders can be easily and effectively prevented or treated. Examples of the neurological disorders include those exemplified in the section of the <<Aquaporin 4 function promotor>>. Among the examples, it is preferable that the pharmaceutical composition for neurological disorders of the present embodiment is used for preventing or treating Alzheimer's disease, a cerebral infarction, a brain tumor, a demyelinating disease, epilepsy, or neuropathic pain.

<Dosage>

The pharmaceutical composition of the present embodiment is appropriately adjusted by considering the age, the sex, the weight, the symptoms, the treatment method, the administration method, the treatment time, and the like of test animals (various mammals including humans and non-human animals, and preferably humans).

In a case where the AQP 4 function promotor contained in the pharmaceutical composition for neurological disorders of the present embodiment is the compound (1), the dosage thereof varies depending on the symptoms. In a case of a normal adult (with a weight of 60 kg) taking this through oral administration, the dosage is considered to be approximately 1 to 20 g, preferably approximately 4 to 12 g, and more preferably approximately 8 to 10 g per day.

In a case of a normal adult (with a weight of 60 kg) taking this through parenteral administration, for example, in an injection form, a single dosage varies depending on the symptoms and the administration method, and it is considered to be suitable that the administration is performed by intravenous injection with a dosage of approximately 0.5 to 10 g, preferably approximately 2 to 5 g, and more preferably approximately 3 to 4 g per day.

In a case where the AQP 4 function promotor contained in the pharmaceutical composition for neurological disorders of the present embodiment is the compound (2), the dosage thereof varies depending on the symptoms. In a case of a normal adult (with a weight of 60 kg) taking this through oral administration, the dosage is considered to be approximately 0.1 to 3 g, preferably approximately 0.5 to 1.5 g, and more preferably approximately 1 to 1.4 g per day.

In a case of a normal adult (with a weight of 60 kg) taking this through parenteral administration, for example, in an injection form, a single dosage varies depending on the symptoms and the administration method, and it is considered to be suitable that the administration is performed by intravenous injection with a dosage of approximately 0.05 to 2 g, preferably approximately 0.3 to 1.5 g, and more preferably approximately 0.5 to 0.8 g per day.

As the administration frequency, it is preferable that the administration is performed one to several times per week on average.

Examples of the administration form include methods known to those skill in the art, such as intraarterial injection, intravenous injection, subcutaneous injection, intranasal administration, intraperitoneal administration, transbronchial administration, intramuscular administration, percutaneous administration, and oral administration. Among these, intravenous injection or intraperitoneal administration is preferable.

An injection can be prepared as a non-aqueous diluent (for example, vegetable oils such as polyethylene glycol and olive oil; and alcohols such as ethanol), a suspension, or an opalizer. Further, sterilization of such an injection can be performed by filter sterilization using a filter or blending a disinfectant or the like. The injection can be produced as the form of prior preparation. In other words, the injection can be used as a sterile solid composition by being dissolved in distilled water for injection or other solvents before use according to a freeze drying method.

<Composition Component>

The pharmaceutical composition of the present embodiment contains a therapeutically effective amount of the carriers described above and physiologically active substances, and a pharmaceutically acceptable carrier or diluent. Examples of the pharmaceutically acceptable carrier or diluent include an excipient, a thinner, a bulking agent, a disintegrant, a stabilizer, a preservative, a buffer, an emulsifier, an aromatic, a colorant, a sweetener, a viscous agent, a corrigent, a solubilizing agent, and an additive. By using one or more of these carriers, a pharmaceutical composition in the form of an injection, a liquid, a capsule, a suspension, an emulsion, or a syrup can be prepared.

Further, a colloidal dispersion system can be used as a carrier. The colloidal dispersion system is expected to have an effect of improving in vivo stability of the above-described AQP 4 function promotor and an effect of improving transferability of the above-described AQP 4 function promotor to a specific organ, tissue, or cell. Examples of the colloidal dispersion system include m polyethylene glycol, a polymer complex, a polymer aggregate, a nanocapsule, a microsphere, a bead, an oil-in-water emulsifier, a micelle, a mixed micelle, and a liposome-containing lipid, and a liposome or a vesicle of an artificial membrane which has an effect of efficiently transporting the above-described AQP 4 function promotor to a specific organ, tissue, or cell is preferable.

Examples of the formulation in the pharmaceutical composition of the present embodiment include those which are orally used as tablets, capsules, elixirs, or microcapsules, coated with sugar as necessary.

In addition, other examples thereof include those which are parenterally used in the form of a sterile solution with water or a pharmaceutically acceptable liquid other than water or an injection of a suspension. Further, those formulated by being combined with the pharmaceutically acceptable carrier or diluent, specifically, sterile water or physiological saline, vegetable oil, an emulsifier, a suspension, a surfactant, a stabilizer, a flavoring agent, an excipient, a vehicle, a preservative, or a binder so as to be mixed in a unit dosage form required for commonly accepted pharmaceutical implementation are also exemplified.

Examples of the additive which can be mixed into a tablet or a capsule include a binder such as gelatin, corn starch, gum tragacanth, or gum arabic; an excipient such as crystalline cellulose; a swelling agent such as corn starch, gelatin, or alginic acid; a lubricant such as magnesium stearate; a sweetener such as sucrose, lactose, or saccharin; and a flavoring agent such as peppermint, akamono oil, or cherry. In a case where a dispensing unit form is a capsule, the above-described material may further contain a liquid carrier such as fats and oils. The sterile composition for injection can be prescribed according to typical formulation implementation using a vehicle such as distilled water for injection.

In a case where the pharmaceutical composition of the present embodiment is an injection, the sterile composition can be prescribed according to typical formulation implementation using a vehicle such as distilled water for injection. Further, examples of an aqueous solution for injection include physiological saline, an isotonic solution containing glucose and other adjuvants such as D-sorbitol, D-mannose, D-mannitol, and sodium chloride, and the aqueous solution may be used together with an appropriate solubilizing agent (for example, alcohol (specifically, ethanol), polyalcohol (such as propylene glycol or polyethylene glycol)) or a non-ionic surfactant (for example, Polysorbate 80 ™, HCO-50).

Further, examples of an oily liquid include sesame oil and soybean oil and the oily liquid may be used together with benzyl benzoate or benzyl alcohol as a solubilizing agent. Further, the oily liquid may be further blended with a buffer (such as a phosphate buffer solution or a sodium acetate buffer solution), a soothing agent (such as procaine hydrochloride), a stabilizer (such as benzyl alcohol or phenol), or an antioxidant. An ampule is typically filled with the prepared injection solution.

An injection can be prepared as a non-aqueous diluent (for example, vegetable oils such as polyethylene glycol and olive oil; and alcohols such as ethanol), a suspension, or an opalizer. Further, sterilization of such an injection can be performed by filter sterilization using a filter or blending a disinfectant or the like. The injections can be produced in the form of prior preparation. In other words, the injection can be used as a sterile solid composition by being dissolved in distilled water for injection or other solvents before use according to a freeze drying method.

The pharmaceutical composition of the present embodiment may be used alone or in combination with other pharmaceutical compositions for neurological disorders.

<Treatment Method>

According to one aspect of the present invention, there is provided a pharmaceutical composition which contains the above-described AQP 4 function promotor for treating neurological disorders.

Further, according to another aspect of the present invention, there is provided a pharmaceutical composition which contains a therapeutically effective amount of the above-described AQP 4 function promotor and a pharmaceutically acceptable carrier or diluent.

Further, according to a still another aspect of the present invention, there is provided a treating agent for neurological disorders which contains the pharmaceutical composition.

Further, according to an even still another aspect of the present invention, there is provided use of the above-described AQP 4 function promotor for producing a treating agent for neurological disorders.

Further, according to an even still another aspect of the present invention, there is provided a method of treating neurological disorders, including administering an effective amount of the above-described AQP 4 function promotor to a patient who needs treatment.

EXAMPLES

Hereinafter, the present invention will be described based on examples, but the present invention is not limited to the following examples.

[Production Example 1] Method of Producing Compound 2A

A compound 2A (2-(phenylsulfonamido)-3-benzyloxy-pyridine) which is a compound selected by performing a computer simulation was produced in the manner described below.

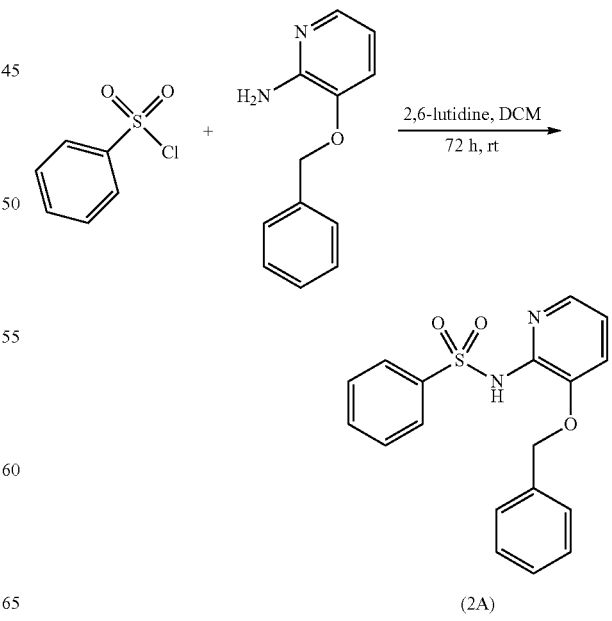

(2A)

First, 2-amino-3-benzyloxypyridine (1.50 g, 7.50 mmol) was added to a 50 mL round bottom flask to which dried dichloromethane (35 mL) had been added. Next, a 2,6-lutidine (2.62 mL, 22.5 mmol) aqueous solution was added to the solution during stirring with a syringe, and a reaction vessel was filled with argon. Next, benzenesulfonyl chloride (1.05 mL, 8.25 mmol) was added to the solution during stirring with a syringe. Subsequently, the reaction was performed while the solution was stirred at room temperature in an argon atmosphere for 72 hours. Next, an obtained yellow solution was washed with a 10% citric acid solution (2×25 mL) and a saturated sodium carbonate solution (2×25 mL). Next, the resultant was dried over magnesium sulfate and filtered, and the moisture was evaporated, thereby obtaining a dark red semi-solid crystal. Next, the obtained dark red crystal was washed with hexane. Subsequently, the resultant was eluted with 33% ethyl acetate/hexane according to a flash chromatography column using silica gel (Wakogel 300), thereby obtaining a white crystal (compound 2A) (yield of 0.309 g, yield coefficient of 13.5%).

The results obtained by analyzing the obtained compound 2A through high performance liquid chromatography (HPLC), high-resolution mass spectra (HR-MS), and $^1$H-NMR are described below.

HPLC: rt=1.72 min (DAD), purity >95% (DAD, ELSD).
HR-MS: anal calc'd for $C_{18}H_{17}N_2O_3S$ (M+H$^+$), 341.0955; found, 341.0932 (9.4 ppm).
$^1$H NMR: δ5.14 ppm, s, 2H; 6.90 ppm, br-t, 1H; 7.29-7.41 ppm, m, 4H; 7.47-7.64 ppm, m, 6H; 7.96 ppm, br-d, J=6.6 Hz, 2H.

Example 1

(1) In Vitro Assay

A reagent used in the in vitro assay was purchased from Sigma-Aldrich Co. LLC or Wako Pure Chemical Industries Ltd. unless otherwise specified and then used as it was.

A Modified Barth's Medium (MBS) was provided to contain NaCl (88 mM), KCl (1 mM), HEPES (10 mM), $MgSO_4$ (0.82 mM), $NaHCO_3$ (2.4 mM), $CaCl_2$ (0.91 mM), $Ca(NO_3)_2$ (0.33 mM), and gentamicin (100 mg/L), prepared to have a pH of 7.5, and used within one week after the preparation.

A buffer solution for separation was provided to contain NaCl (108 mM), KCl (2 mM), EDTA (2 mM), and HEPES (10 mM) and prepared to have a pH of 7.5.

(1-1) Preparation of Oocytes

Isolation, preparation, and transfection of the oocytes of a *Xenopus laevis* were performed using a method described in the reference (Sakimura, et al., FEBS Lett., 272, 73 to 80, 1990.). Specifically, the oocytes were extracted from a female adult of a *Xenopus laevis* (weight of 150 g) and transferred to an MBS. Next, the oocytes were partially transferred to an isolation buffer solution, and the theca folliculi was manually removed so that the oocytes were exposed. Thereafter, the oocytes from which the membrane had been removed were transferred to a fresh MBS and equilibrated for 2 hours before microinjection.

(1-2) Preparation of AQP 4 mRNA Expression Vector

Next, cDNA (SEQ ID NO: 1) encoding human AQP 4 (hAQP 4)-M23 isoform was cloned by a revers transcription polymerase chain reaction (RT-PCR), and the first strand of cDNA was synthesized using an Advantage RT-for-PCR kit (manufactured by Clontech Laboratories, Inc.) from human cerebellar total RNA. PCR primers were designed based on the known base sequences of hAQP 4-4M23. The base sequences of the forward primer and the reverse primer were respectively SEQ ID NO: 2 and SEQ ID NO: 3. Further, mRNA of hAQP 4-M23 was subcloned into the pSP35T expression vector in order to be introduced into the oocytes of a *Xenopus laevis*.

(1-3) Microinjection into Oocytes

Microinjection of the hAQP 4-M23 mRNA expression vector prepared in the section of (1-2) was performed using a Drummond microinjection system. 30 nL of the hAQP 4-M23 mRNA expression vector (3 ng of the mRNA expression vector was injected into one oocyte) or water as a negative control were injected into the oocytes. The oocytes into which the expression vector or water had been injected were cultures in the MBS at 20° C. for 30 minutes.

(1-4) Administration of Candidate Compound

Next, four or five oocytes were transferred to 48-well plates (Costar 3526) together with 450 μL of the MBS after 48 hours from the injection. Subsequently, before 30 minutes of the assay, a solution (50 μL) containing 200 μM of a candidate compound (the compound 2A prepared in Production Example 1) in a 1% DMSO aqueous solution (manufactured by Sigma-Aldrich Co. LLC, Hibri-Max) or a blank (1% DMSO) was fractionated and administered to the oocytes. The final concentration of the culture medium was 20 μM in a case of the candidate compound (the compound 2A prepared in Production Example 1) and 0.1% in a case of the DMSO.

Next, the transferred oocytes were imaged using an SZX 16 microscope (manufactured by Olympus Corporation) connected to a DP 26 digital camera (manufactured by Olympus Corporation). The temperature of the plate was set to 24° C. using a MATS-5555 temperature adjustment stage (manufactured by TOKAI HIT Co., Ltd.). A Hypotonic reagent (1000 μL) was added, and an assay initial image (t=3 seconds) and images at 15 second intervals of were recorded up to 250 seconds after the administration. The oocytes died before 250 seconds passed were removed from the analysis.

(1-5) Analysis of Volume of Oocytes

Subsequently, the images were transferred to a personal computer, and the region of each oocyte was evaluated using NIH Image-J. The value of the cross-sectional area of each oocyte in a plurality of equally determined measurement times was converted into a volume assumed to be spherical. At least five (n=5) oocytes of the relative volumes compared to the initial images of the oocytes at each time point were averaged to acquire a standard deviation. The results obtained by performing administration of the compound 2A are shown in FIG. 1. In FIG. 1, "Sham" indicates the oocyte into which water was injected, "Blank" indicates the oocyte into which mRNA of AQP 4 was injected and a compound was not administered, and "Compound 2A" indicates the oocyte into which mRNA of AQP 4 was injected and the compound 2A was administered.

As shown in FIG. 1, it was verified that the volume of the oocyte to which the compound 2A was administered was significantly increased. Based on this result, it was speculated that water was taken into the oocytes so that the volume of the compound 2A was increased by promoting the function of the AQP 4.

[Test Example 1] AQP 4 Function Promotion Verification Test Using Mice (1) Administration of Candidate Compound to Mice Normal male B6SJL-Tg mice obtained from Jackson Laboratory were bred until 8 weeks old. Next, indomethacin as a comparative example, the compound 2A prepared in Production Example 1, and physiological saline as the control were intraperitoneally administered to respectively five mice.

Figure 2A:
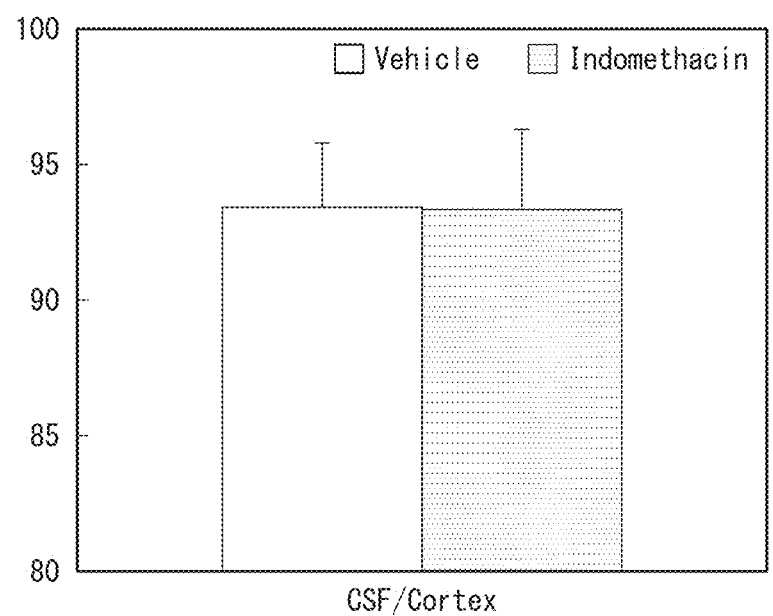
FIG. 2A is a graph showing the results obtained by measuring a change in the function of the AQP 4 in the brain of a mouse to which indomethacin has been administered in Test Example 1.
Figure 2B:
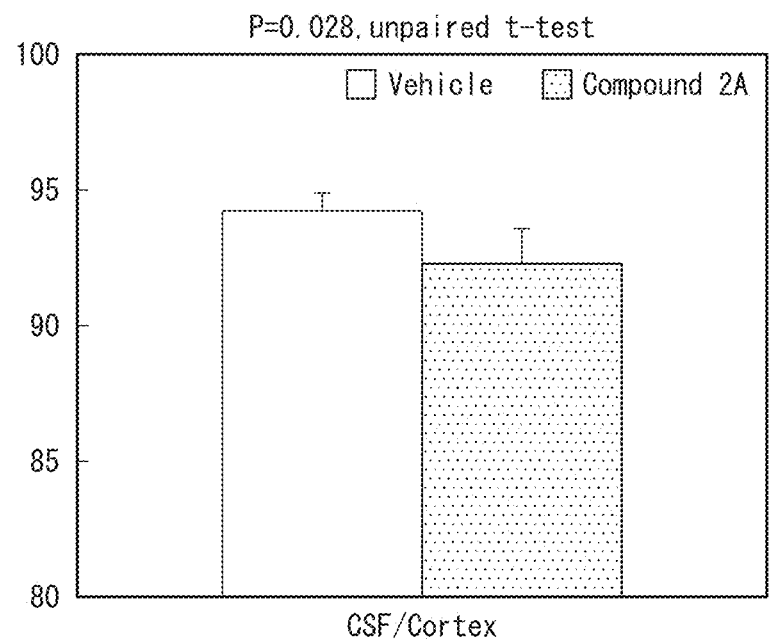
FIG. 2B is a graph showing the results obtained by measuring a change in the function of the AQP 4 in the brain of a mouse to which a compound 2A has been administered in Test Example 1.

Thereafter, 0.2 mL of typical physiological saline containing 20% $H_2^{17}O$ was administered to the right femoral vein of each mouse through the PE10 tube inserted thereinto using an automatic syringe at 0.04 mL/sec. Next, images showing the dynamics of $H_2^{17}O$ in the brain of each mouse ((cortex) and the cerebrospinal fluid (CSF)) at 8 second intervals were recorded until 70 seconds after the administration using magnetic resonance imaging (MRI). The results are shown in FIG. 2A (administration of indomethacin) and FIG. 2B (administration of compound 2A). FIGS. 2A and 2B show relative values (CSF/Cortex) of CSF with respect to the cortex. In FIGS. 2A and 2B, "Vehicle" indicates a non-administration control group, "Indomethacin" indicates an indomethacin administration group, and "Compound 2A" indicates a compound 2A administration group.

In FIGS. 2A and 2B, the numerical values of CSF/Cortex were decreased in the mice to which the compound 2A was administered, and water discharge (flow of cerebrospinal fluid) was improved. Based on this result, it was speculated that the compound 2A was able to directly act on the AQP 4 to promote the function thereof.

[Test Example 2] AQP 4 Function Promotion Verification Test Using Alzheimer's Disease Model Mice (1) Preparation of Candidate Compound The compound 2A prepared in Production Example 1 and 2-guanidino-1-ethanesulfonic acid (guanidinoethyl sulfonate; GES) (hereinafter, also referred to as a "compound 1A") obtained from the following reaction formula were produced by entrusting the production and then used.

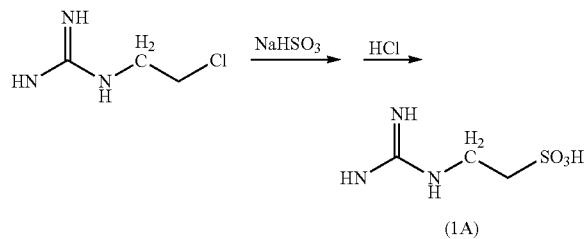

(1A)

(2) Administration of Candidate Compound to Mice

5×FAD Alzheimer's disease model mice were bred until 4 months old. Next, the compound 1A (50 mg/kg) or the compound 2A (200 mg/kg) prepared in Production Example 1 were orally administered to the mice for 3 months. Further, a non-administration group was also prepared as the control.

(3) Dynamics of $H_2^{17}O$ in Brain of Mouse (Cortex and CSF) Using MRI

Figure 3:
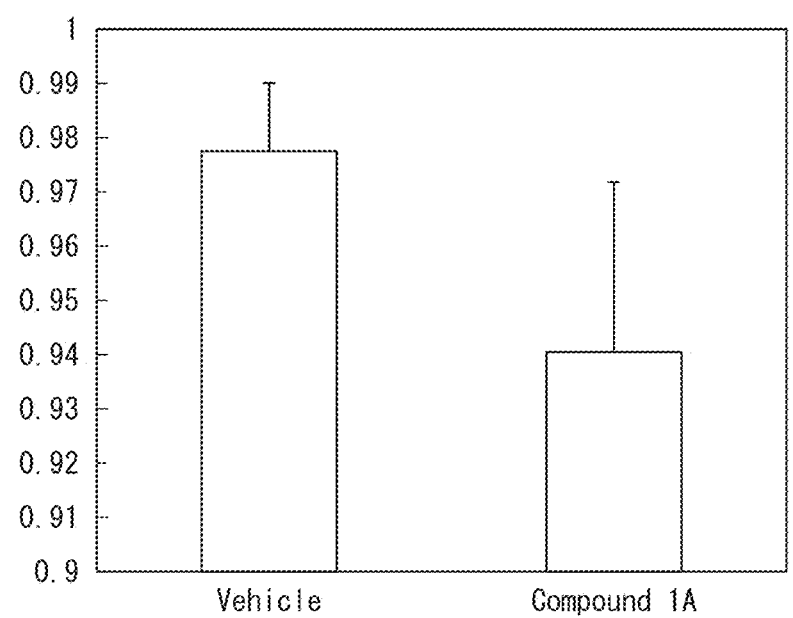
FIG. 3 is a graph showing the results obtained by measuring a change in the function of the AQP 4 in the brain of a mouse to which a compound 1A has been administered in Test Example 2.

With respect to the group of mice to which the compound 1A was administered and the non-administration group, images showing the dynamics of $H_2^{17}O$ in the brain of each mouse (cortex and CSF) at 8 second intervals were recorded until 70 seconds after the administration using MRI according to the same method as in Test Example 1. The results are shown in FIG. 3. In FIG. 3, "Vehicle" indicates a non-administration group and "Compound 1A" indicates a compound 1A administration group. Further, relative values (CSF/Cortex) with respect to the cortex are also shown.

As shown in FIG. 3, it was clarified that the AQP 4 function was markedly promoted in the Alzheimer's disease mice to which the GES was administered. Based on this mechanism, it was speculated that the function of AQP 4 was promoted and enhanced due to an ion buffering action in the perivascular space.

(4) Immunostaining of Brain

Subsequently, the brain was extracted from each mouse, paraffin-embedded slices (respectively with a thickness of 4 μm) were prepared using brain tissues, and immunohistochemical staining was performed according to the following method.

Figure 4A:
FIG. 4A shows images obtained by staining Aβ 42 using brain slices of a non-administration group, a compound 1A administration group, and a compound 2A administration group in Test Example 2.
Figure 5A:
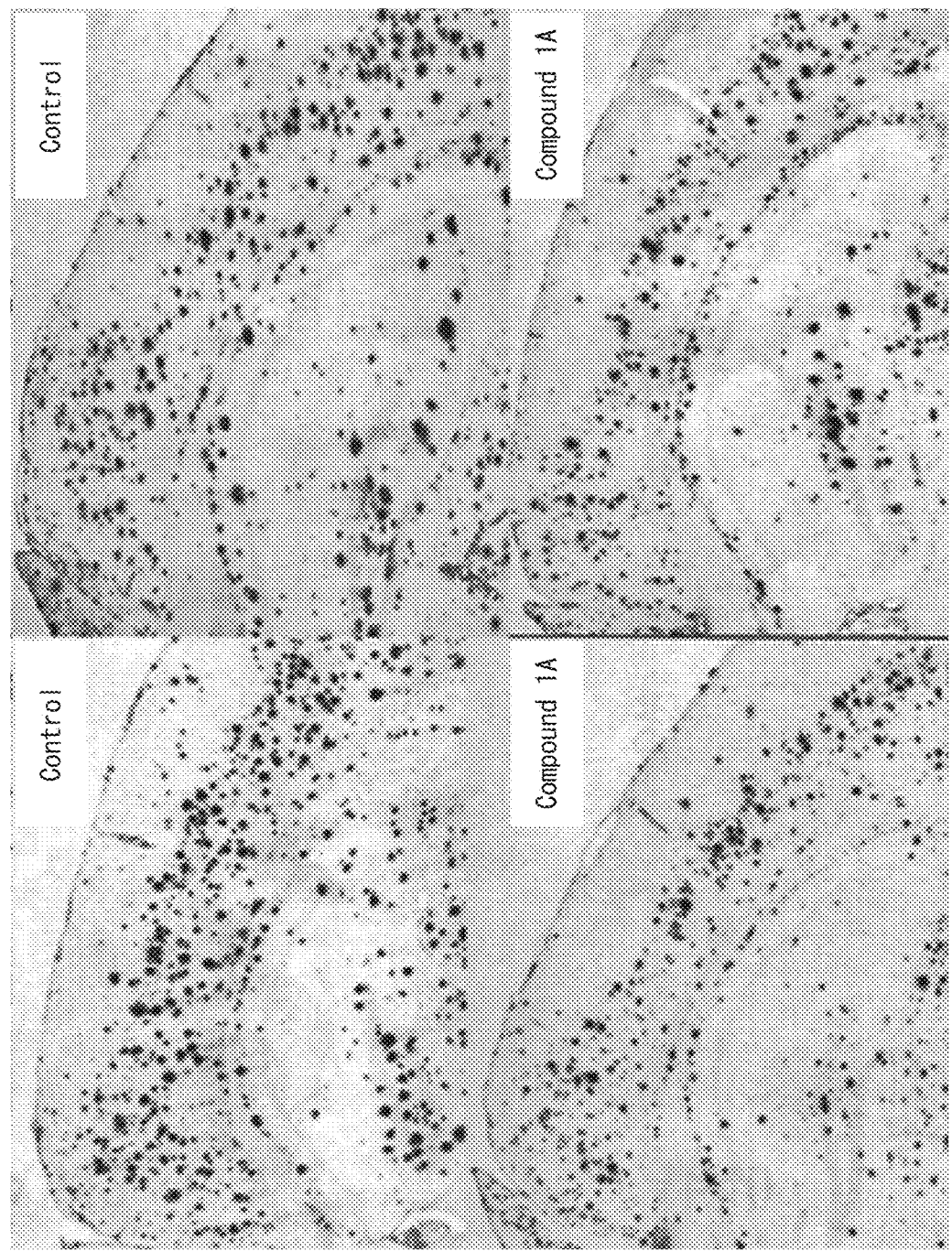
FIG. 5A shows images obtained by staining total Aβ using brain slices of the non-administration group and the compound 1A administration group in Test Example 2.
Figure 6A:
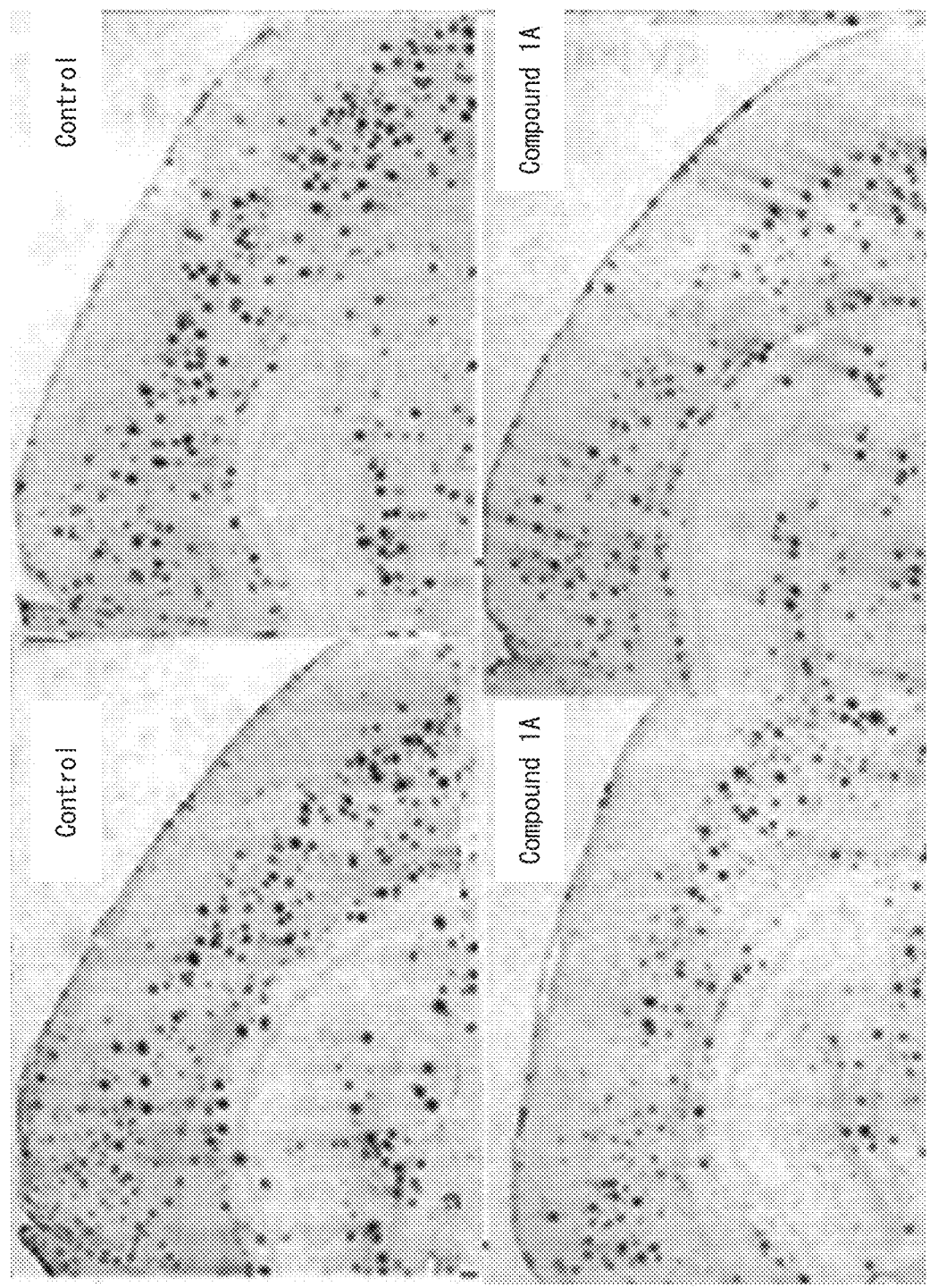
FIG. 6A shows images obtained by staining Aβ 40 using brain slices of the non-administration group and the compound 1A administration group in Test Example 2.
Figure 7A:
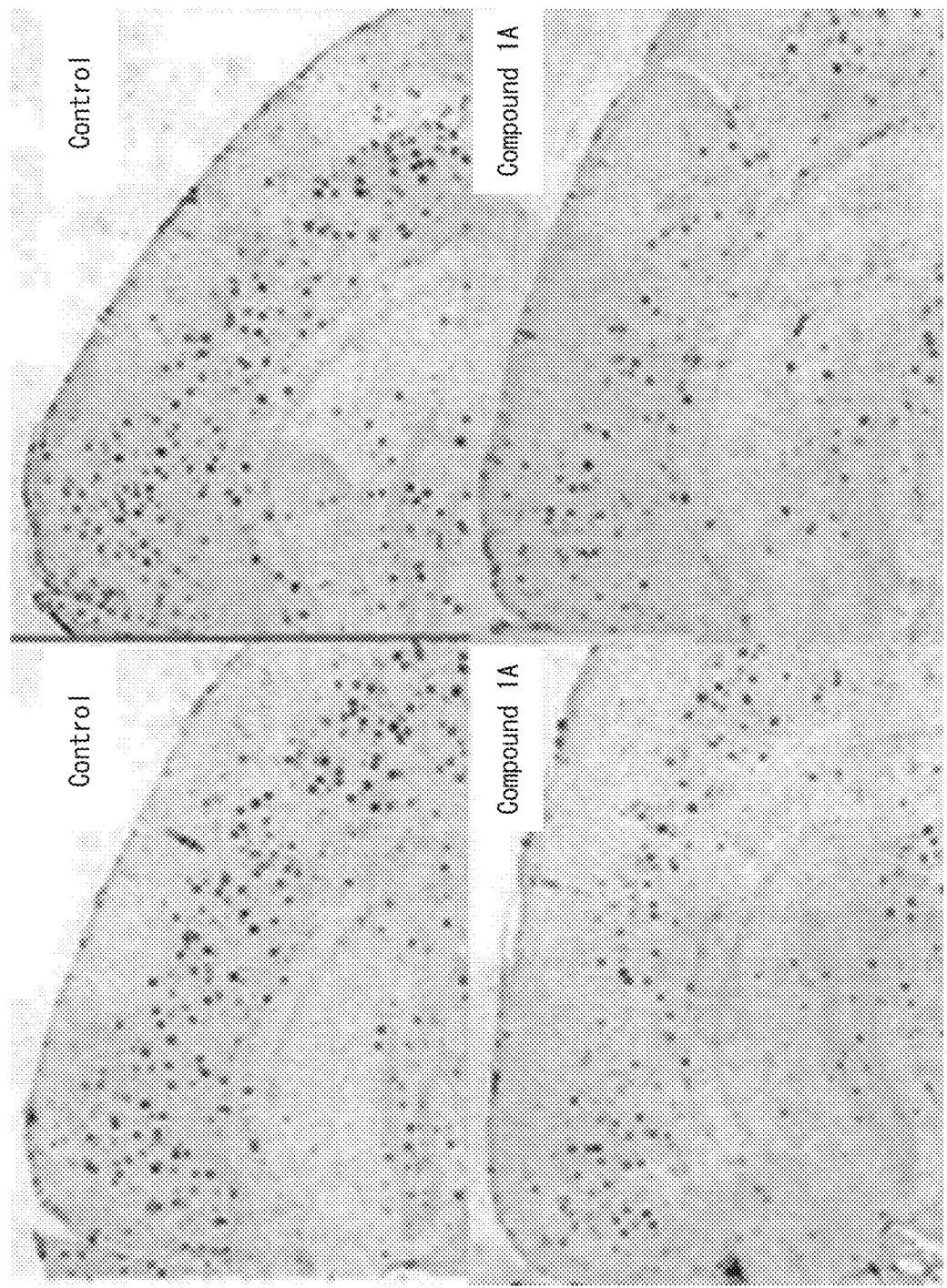
FIG. 7A shows images obtained by staining Aβ 42 using brain slices of the non-administration group and the compound 1A administration group in Test Example 2.

First, the slices were subjected to a formic acid treatment, and overnight incubation was performed at 4° C. using [1] Mouse monoclonal Anti-Human Amyloid β (Total Aβ) (10027, IBL, Japan), [2] Rabbit polyclonal Anti-Human Amyloid β1-40 (AJ340) (18580, IBL, Japan), or [3] Rabbit polyclonal Anti-Human Amyloid β1-42 (AJ342) (18582, IBL, Japan) as primary antibodies. Further, the dilution ratios of antibodies were respectively [1]×50, [2]×200, and [3]×200. After the secondary antibodies were applied, the antibodies were visualized according to a polymer method using Histofine DAB substrate kit (NICHIREI CORPORATION, JAPAN). FIG. 5A shows images obtained by staining total Aβ using brain slices of the non-administration group and the compound 1A administration group, FIG. 6A shows images obtained by staining Aβ 40 using brain slices of the non-administration group and the compound 1A administration group, FIG. 4A shows images obtained by staining Aβ 42 using brain slices of the non-administration group, the compound 1A administration group, and the compound 2A administration group, and FIG. 7A shows images obtained by staining Aβ 42 using brain slices of the non-administration group and the compound 1A administration group.

In FIGS. 4A to 7A, "Control" indicates the non-administration group, "Compound 1A" indicates the compound 1A administration group, and "Compound 2A" indicates the compound 2A administration group.

(5) Quantification of Senile Plaques

Figure 5B:
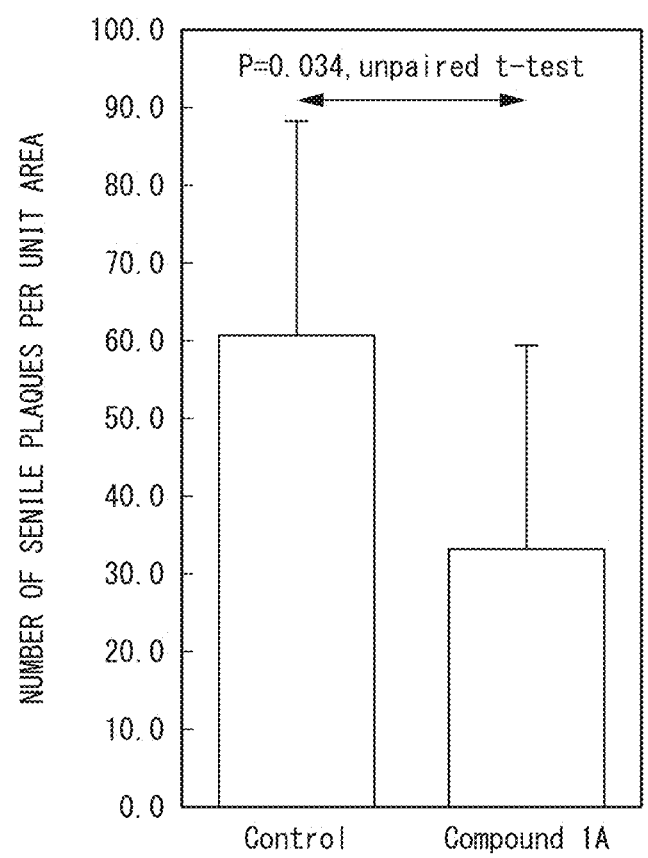
FIG. 5B is a graph showing quantitative results of senile plaques from the images obtained by staining total Aβ using brain slices of the non-administration group and the compound 1A administration group in Test Example 2.
Figure 6B:
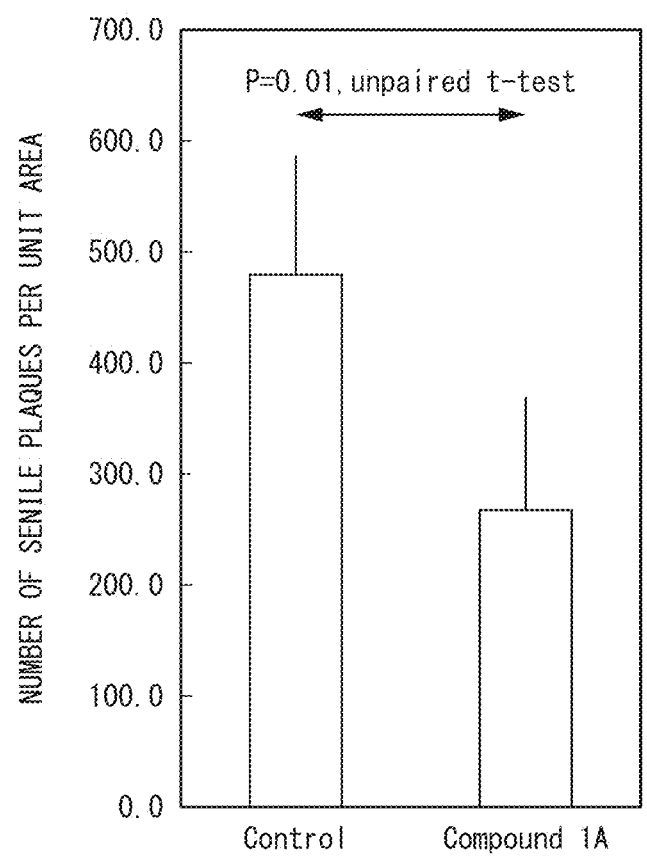
FIG. 6B is a graph showing quantitative results of senile plaques from the images obtained by staining Aβ 40 using brain slices of the non-administration group and the compound 1A administration group in Test Example 2.
Figure 7B:
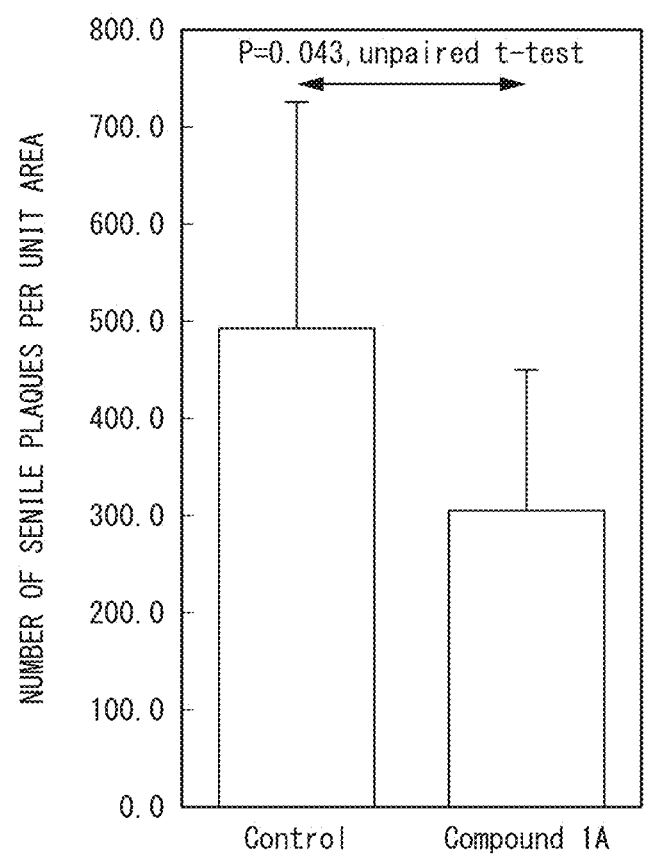
FIG. 7B is a graph showing quantitative results of senile plaques from the images obtained by staining Aβ 42 using brain slices of the non-administration group and the compound 1A administration group in Test Example 2.

Next, the tissue images of the stained samples were imaged using a bright field optical microscope (Olympus Corporation, BX53, DP73), and the images were stored according to the TIFF format (2400×1800 pixels, 3.5×2.6 mm, 2.13 μm²/pixel). Each image was analyzed in the following manner using a particle analysis function of the image analysis processing software (Aquacosmos, Hamamatsu Photonics K.K., Japan). ROI was set as the cerebral cortex, particles were extracted according to a binarization method, and the area (the number of pixels) of each extracted particle was automatically calculated and output. In output particle data, particles with an area of 10 pixels or less were removed as noise and quantified. FIG. 5B shows quantitative results of senile plaques from the images obtained by staining total Aβ using brain slices of the non-administration group and the compound 1A administration group, FIG. 6B shows quantitative results of senile plaques from the images obtained by staining Aβ 40 using brain slices of the non-administration group and the compound 1A administration group, FIG. 4B shows quantitative results of senile plaques from the images obtained by staining Aβ 42 using brain slices of the non-administration group, the compound 1A administration group, and the compound 2A administration group, and FIG. 7B shows quantitative results of senile plaques from the images obtained by staining Aβ 42 using brain slices of the non-administration group and the compound 1A administration group.

In FIGS. 4B to 7B, "Control" indicates the non-administration group, "Compound 1A" indicates the compound 1A administration group, and "Compound 2A" indicates the compound 2A administration group.

Amyloid β (Aβ) is considered to be a direct cause of Alzheimer's disease, and the center of this disorder is Aβ 42 which is hydrophobic and easily aggregated. In animal tests, there have been many reports related to chemical agents that reduce hydrophilic Aβ 40, but there have been few reports related to chemical agents that significantly reduce Aβ 42. Further, the total number of senile plaques includes both of Aβ 40 and Aβ 42.

Figure 4B:
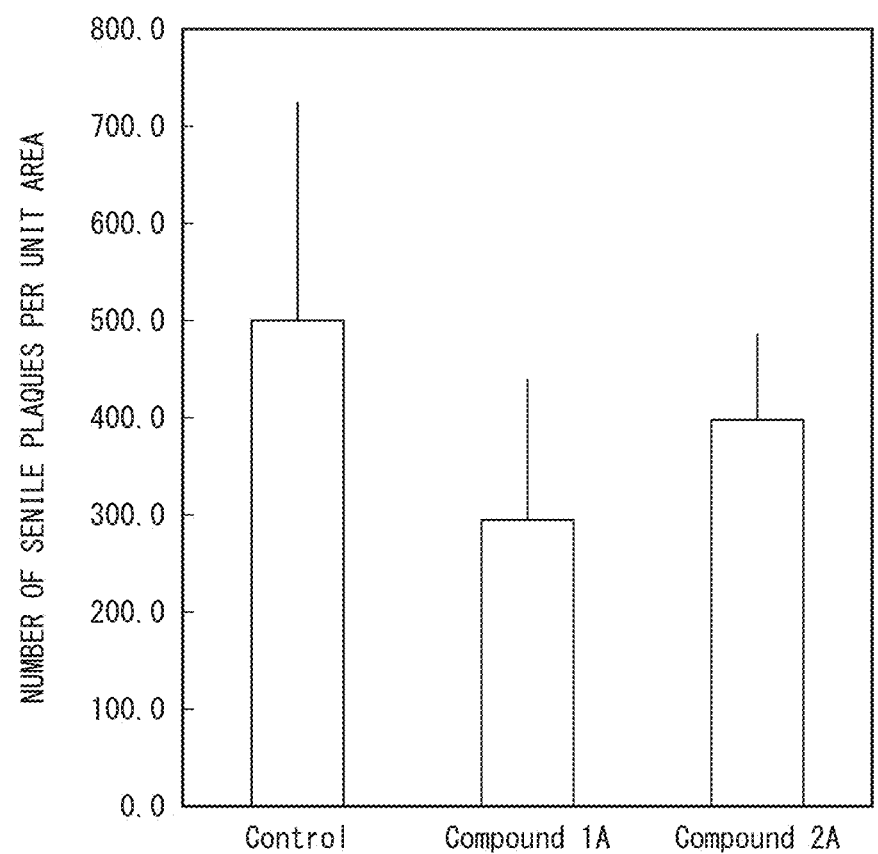
FIG. 4B is a graph showing quantitative results of senile plaques from the images obtained by staining Aβ 42 using brain slices of the non-administration group, the compound 1A administration group, and the compound 2A administration group in Test Example 2.

As shown in FIGS. 4A and 4B, it was clarified that an increase in senile plaques formed of Aβ 42 which is the cause of nerve dropout in Alzheimer's disease model mice can be suppressed by orally administering the compound 1A and the compound 2A.

As shown in FIGS. 5A, 5B, 6A, 6B, 7A, and 7B, it was clarified that an increase in senile plaques of Alzheimer's disease model mice can be suppressed by orally administering the compound 1A.

INDUSTRIAL APPLICABILITY

The Aquaporin 4 function promotor of the present embodiment is a novel aquaporin 4 function promotor which has an action of directly promoting the function of the AQP 4 and is useful for treating disorders.

What is claimed is:

1. A method of treating a neurological disorder in a subject in need thereof, comprising administering to the subject a therapeutically effective amount of a pharmaceutical composition comprising
an aquaporin 4 function promotor comprising:
a compound represented by Formula (2) or a pharmaceutically acceptable salt thereof, as an active ingredient;

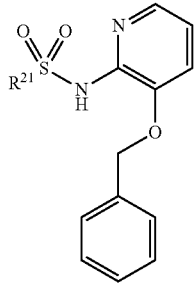

(2)

wherein $R^{21}$ is selected from the group consisting of an alkyl group having 1 to 10 carbon atoms, an alicyclic heterocyclic group, an aromatic hydrocarbon group, and an aromatic heterocyclic group; and at least one pharmaceutically acceptable carrier or pharmaceutically acceptable diluent, wherein the neurological disorder is selected from the group consisting of Alzheimer's disease, a cerebral infarction, and a brain tumor.

2. The method of treating a neurological disorder in a subject in need thereof according to claim 1, wherein $R^{21}$ is selected from the group consisting of methyl, ethyl, n-propyl, i-propyl, n-butyl, i-butyl, sec-butyl, n-pentyl, i-pentyl, n-hexyl, cyclopropyl, cyclobutyl, cyclopentyl, cyclohexyl, 2-pyrrolidinyl, 3-pyrrolidinyl, 2-tetrahydrofuranyl, 3-tetrahydrofuranyl, 2-pyrrolyl, 3-pyrrolyl, 2-furanyl, and 3-furanyl.

3. The method of treating a neurological disorder in a subject in need thereof according to claim 1, wherein the compound is 2-phenylsulfoamido-3-benzyloxypyrimidine.

* * * * *

SEQUENCE LISTING

<160> NUMBER OF SEQ ID NOS: 3

<210> SEQ ID NO 1
<211> LENGTH: 1106
<212> TYPE: DNA
<213> ORGANISM: Homo sapiens

<400> SEQUENCE: 1

```
gagaacatca tggtggcttt caaaggggtc tggactcaag ctttctggaa agcagtcaca      60
gcggaatttc tggccatgct tatttttgtt ctcctcagcc tgggatccac catcaactgg     120
ggtggaacag aaaagccttt accggtcgac atggttctca tctcccttg ctttggactc     180
agcattgcaa ccatggtgca gtgctttggc catatcagcg gtggccacat caaccctgca     240
gtgactgtgg ccatggtgtg caccaggaag atcagcatcg ccaagtctgt cttctacatc     300
gcagcccagt gcctgggggc catcattgga gcaggaatcc tctatctggt cacacctccc     360
agtgtggtgg gaggcctggg agtcaccatg gttcatggaa atcttaccgc tggtcatggt     420
ctcctggttg agttgataat cacatttcaa ttggtgttta ctatctttgc cagctgtgat     480
tccaaacgga ctgatgtcac tggctcaata gctttagcaa ttggattttc tgttgcaatt     540
ggacatttat ttgcaatcaa ttatactggt gccagcatga atcccgcccg atcctttgga     600
cctgcagtta tcatgggaaa ttgggaaaac cattggatat attgggttgg gcccatcata     660
ggagctgtcc tcgctggtgg cctttatgag tatgtcttct gtccagatgt tgaattcaaa     720
cgtcgtttta aagaagcctt cagcaaagct gcccagcaaa caaaaggaag ctacatggag     780
gtggaggaca acaggagtca ggtagagacg gatgacctga ttctaaaacc tggagtggtg     840
catgtgattg acgttgaccg gggagaggag aagaagggga agaccaatc tggagaggta     900
ttgtcttcag tatgactaga agatcgcact gaaagcagac aagactcctt agaactgtcc     960
tcagatttcc ttccacccat taaggaaaca gatttgttat aaattagaaa tgtgcaggtt    1020
tgttgtttca tgtcatatta ctcagtctaa acaataaata tttcataatt tacaaaggag    1080
gaacggaaga aacctattgt gaattc                                         1106
```

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA

<400> SEQUENCE: 2

```
cagtaagtgt ggacctttgt                                                  20
```

```
<210> SEQ ID NO 3
<211> LENGTH: 20
<212> TYPE: DNA
<213> ORGANISM: Artificial Sequence
<220> FEATURE:
<223> OTHER INFORMATION: Synthetic DNA

<400> SEQUENCE: 3
tcatactgaa gacaatacct                                              20
```